US010569064B2

(12) United States Patent
Vase et al.

(10) Patent No.: US 10,569,064 B2
(45) Date of Patent: Feb. 25, 2020

(54) DEVICES AND METHODS FOR PROVIDING FOCAL COOLING TO THE BRAIN AND SPINAL CORD

(71) Applicant: MINNETRONIX, INC., St. Paul, MN (US)

(72) Inventors: Abhi Vase, Los Altos Hills, CA (US); Don W. E. Evans, St. Paul, MN (US)

(73) Assignee: MINNETRONIX, INC., St. Paul, MN (US)

( * ) Notice: Subject to any disclaimer, the term of this patent is extended or adjusted under 35 U.S.C. 154(b) by 163 days.

(21) Appl. No.: 15/287,174

(22) Filed: Oct. 6, 2016

(65) Prior Publication Data

US 2017/0095649 A1    Apr. 6, 2017

Related U.S. Application Data

(60) Provisional application No. 62/237,867, filed on Oct. 6, 2015.

(51) Int. Cl.
*A61M 27/00* (2006.01)
*A61M 25/00* (2006.01)
*A61F 7/12* (2006.01)

(52) U.S. Cl.
CPC ............ *A61M 27/006* (2013.01); *A61F 7/12* (2013.01); *A61M 25/007* (2013.01);
(Continued)

(58) Field of Classification Search
CPC ......... A61M 27/006; A61F 7/00; A61F 7/123; A61F 7/12
See application file for complete search history.

(56) References Cited

U.S. PATENT DOCUMENTS

| 4,904,237 | A | 2/1990 | Janese |  |
|---|---|---|---|---|
| 7,318,834 | B2 * | 1/2008 | Njemanze | A61F 7/12 607/105 |

(Continued)

FOREIGN PATENT DOCUMENTS

| JP | 2013539387 A | 10/2013 |
| WO | 0139819 A2 | 6/2001 |
| WO | 2012027641 A2 | 3/2012 |

OTHER PUBLICATIONS

International Search Report and the Written Opinion dated Feb. 15, 2017 from the International Application No. PCTUS2016055724.

*Primary Examiner* — Nathan R Price
*Assistant Examiner* — Melissa A Snyder
(74) *Attorney, Agent, or Firm* — Seager, Tufte & Wickhem, LLP

(57) ABSTRACT

Systems and methods for systems and methods for focal cooling of the brain and spinal cord are disclosed. Some embodiments may be directed to a neuroprotection system that includes a cerebrospinal fluid processing platform. Embodiments may provide rapid and selective spinal cord hypothermia and drainage. Embodiments may be tailored to selective spinal cord cooling, pressure monitoring and automated drainage. Embodiments may enable local hypothermic neuroprotection, limit the stress of systemic cooling, minimize secondary neuronal damage and achieve maximal neuroprotection while at the same time improving workflow as a result of automated drainage. Embodiments may include a multi-lumen catheter, a drainage collection reservoir bag, a pump to circulate coolant, sensor hardware and controllers to modulate the flow of a heat transfer fluid for cooling to modulate therapeutic hypothermia and re-warming. Certain embodiments may include extracorporeal cooling of cerebrospinal fluid (CSF). Certain embodiments may include circulating heat transfer fluid within a CSF-containing space near the brain or spinal cord using a catheter. Particular methods may be used to determine the length and amount of cooling.

19 Claims, 18 Drawing Sheets

(52) U.S. Cl.
CPC . *A61M 25/0026* (2013.01); *A61M 2202/0464* (2013.01); *A61M 2205/3327* (2013.01); *A61M 2205/3331* (2013.01); *A61M 2205/3368* (2013.01); *A61M 2205/3606* (2013.01); *A61M 2205/7545* (2013.01); *A61M 2210/0693* (2013.01); *A61M 2210/1003* (2013.01); *A61M 2210/127* (2013.01)

(56) References Cited

U.S. PATENT DOCUMENTS

| | | | |
|---|---|---|---|
| 8,435,204 B2 | 5/2013 | Lad et al. | |
| 2002/0077682 A1* | 6/2002 | Lee | A61F 7/12 607/113 |
| 2002/0198579 A1 | 12/2002 | Khanna | |
| 2003/0130651 A1* | 7/2003 | Lennox | A61F 7/12 606/21 |
| 2004/0138728 A1* | 7/2004 | Wong | A61F 7/123 607/105 |
| 2004/0147987 A1* | 7/2004 | Ginsburg | A61F 7/12 607/106 |
| 2006/0161107 A1* | 7/2006 | Mantle | A61F 7/12 604/113 |
| 2010/0305492 A1* | 12/2010 | Lad | A61M 27/006 604/9 |
| 2013/0030411 A1* | 1/2013 | Kreck | A61F 7/12 604/514 |
| 2014/0066830 A1 | 3/2014 | Lad et al. | |
| 2014/0358183 A1* | 12/2014 | Saunders | A61B 17/7002 606/279 |
| 2016/0051801 A1 | 2/2016 | Vase | |

\* cited by examiner

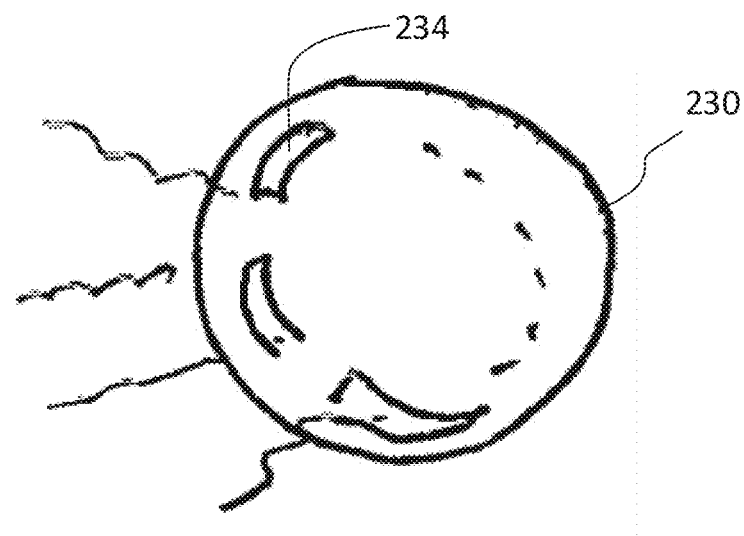
FIG. 8
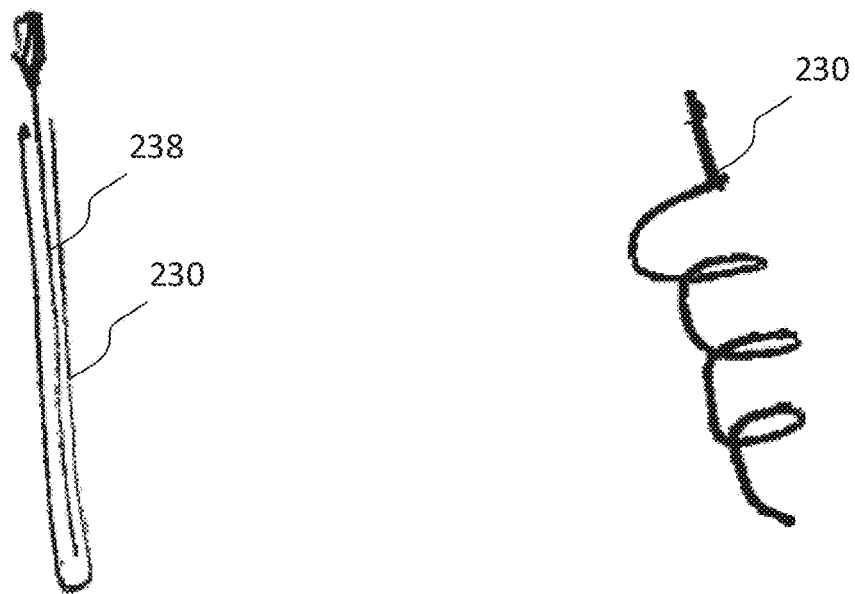
FIG. 9
FIG. 10

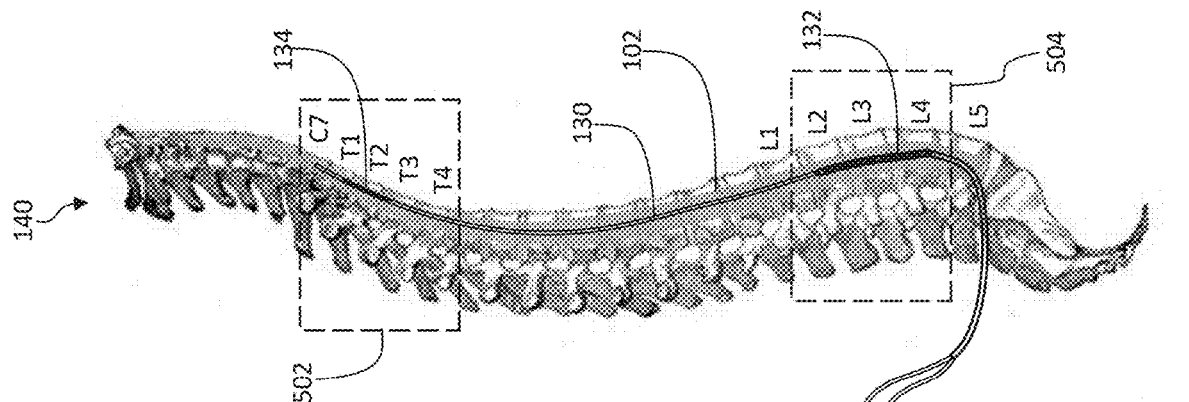
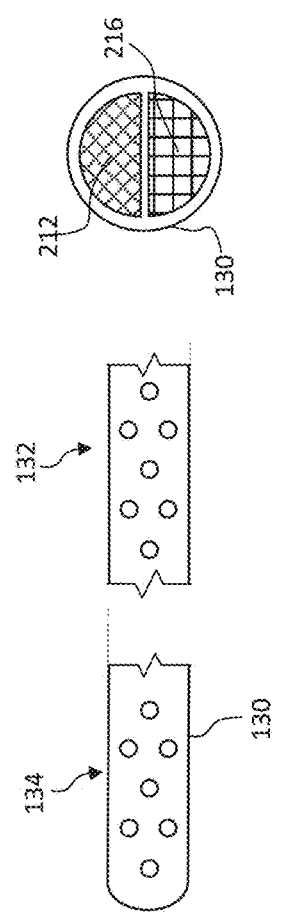
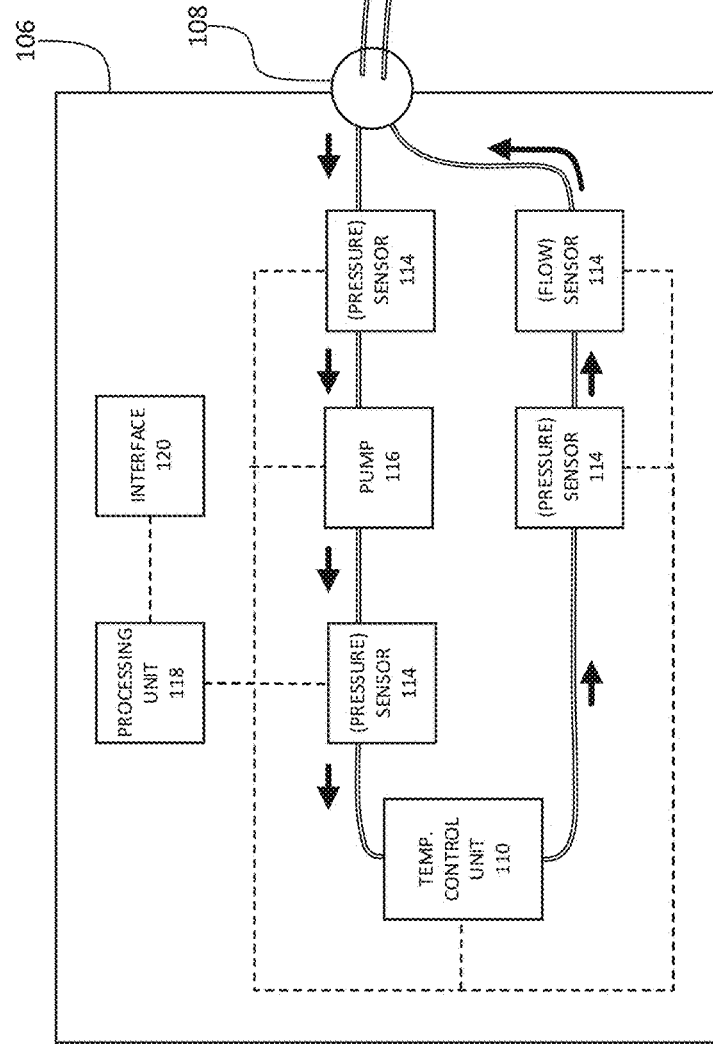
FIG. 19
FIG. 20
FIG. 21

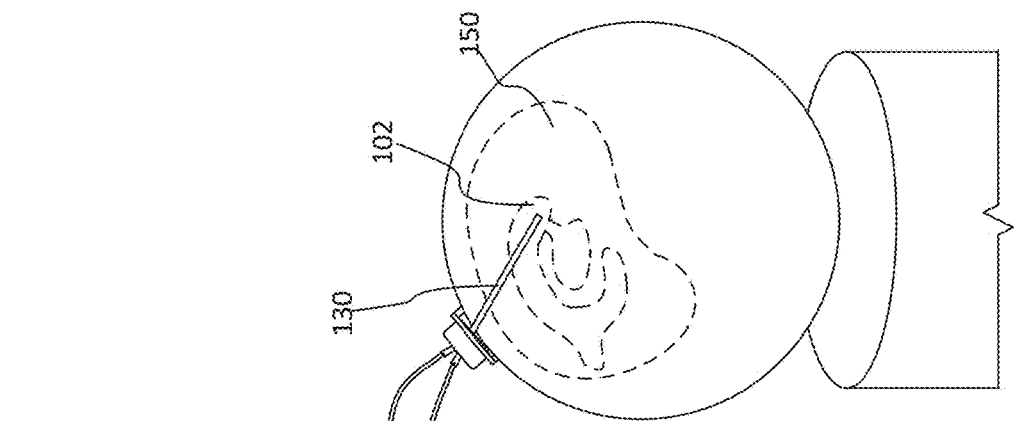
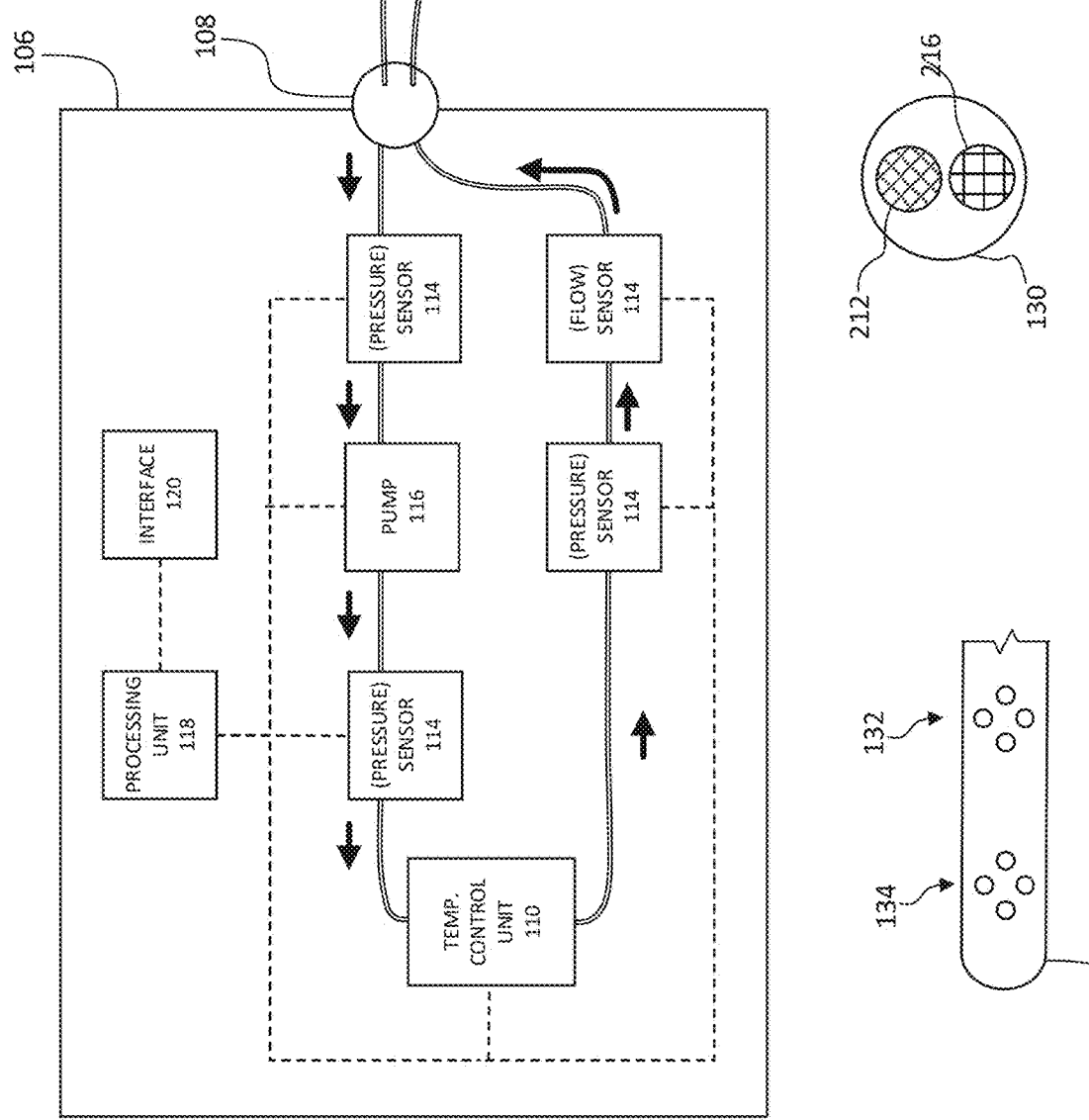
FIG. 22
FIG. 24
FIG. 23

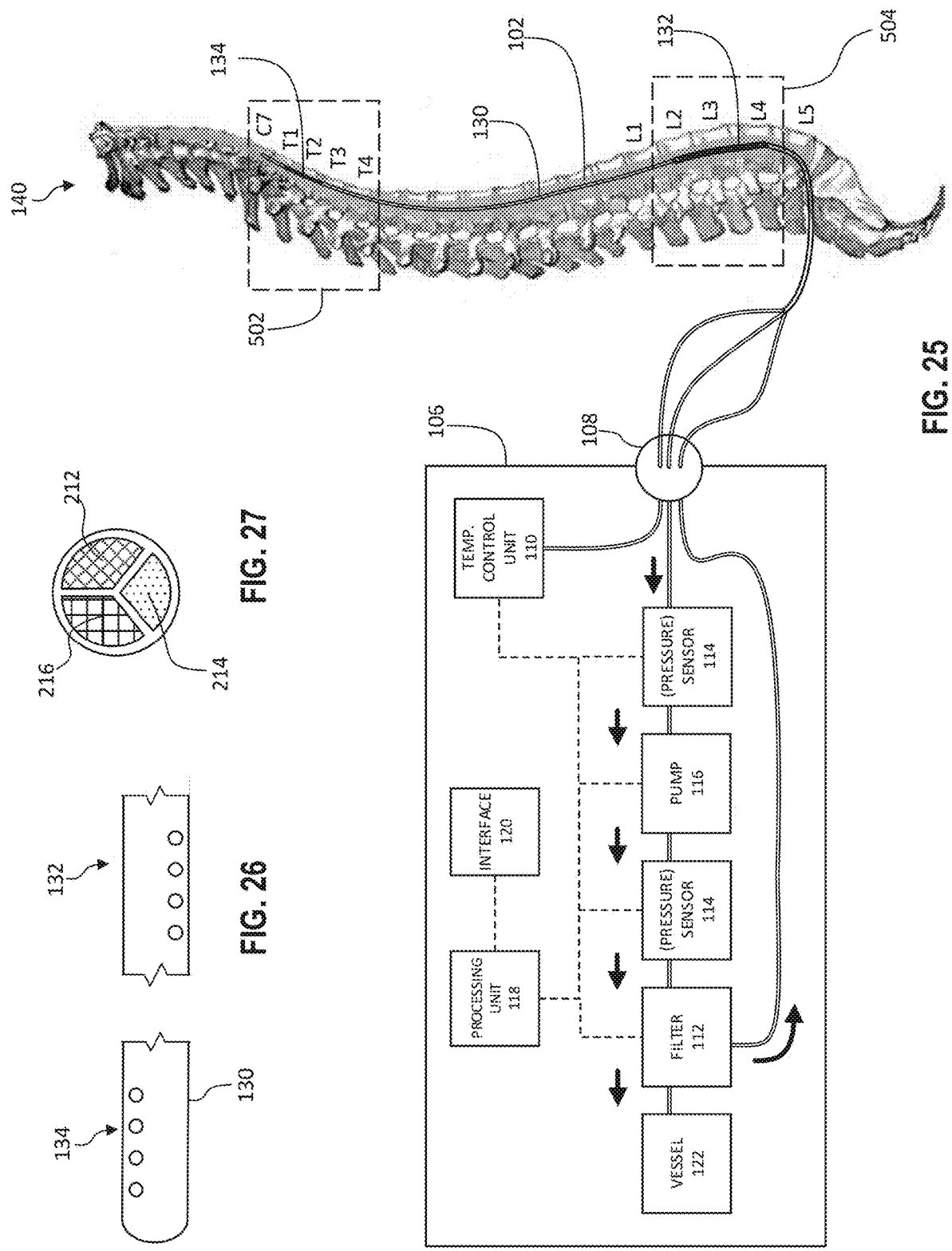

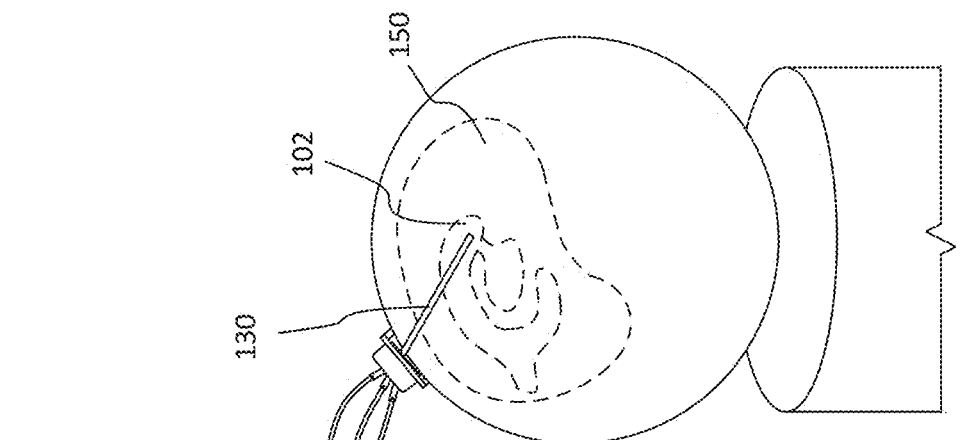
FIG. 28
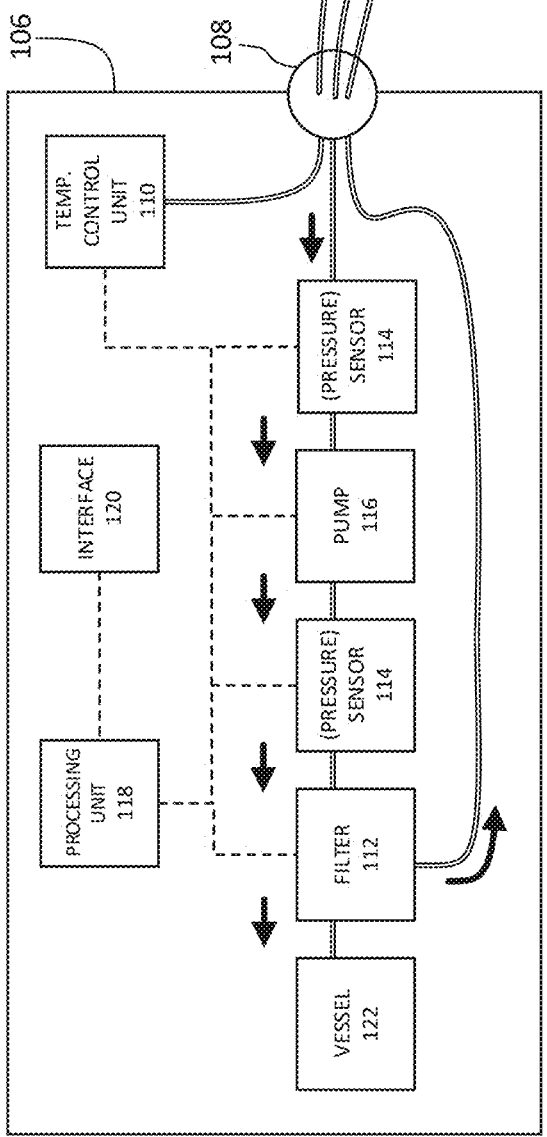
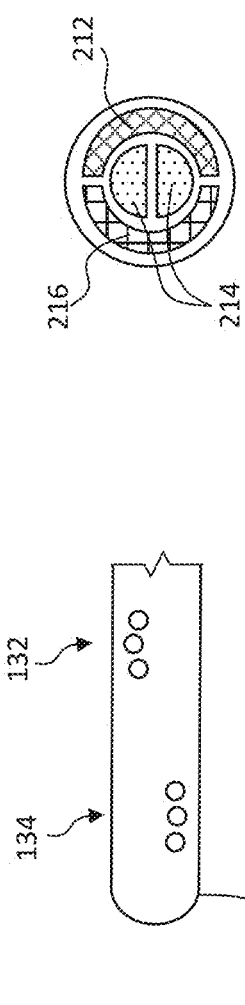
FIG. 30
FIG. 29

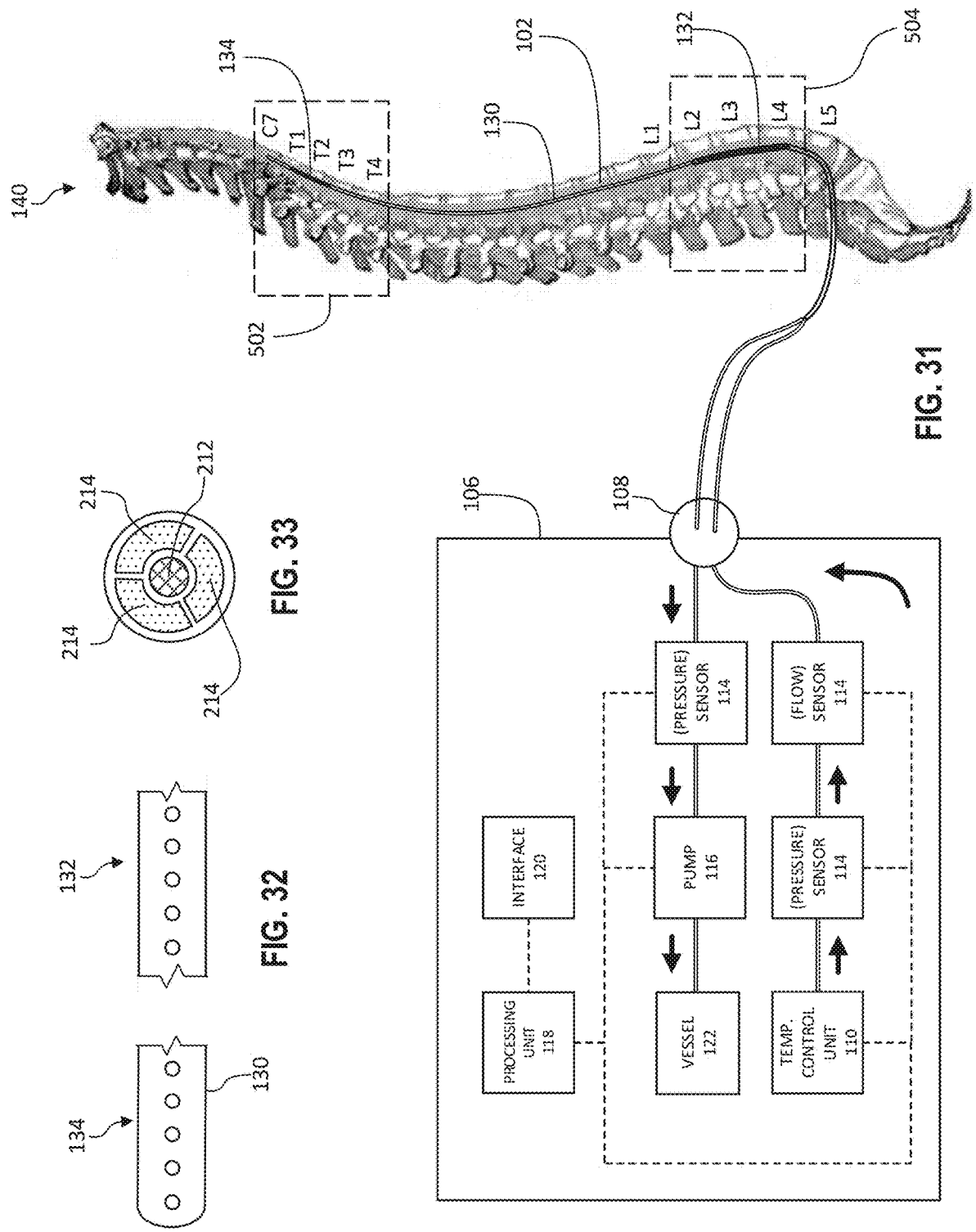

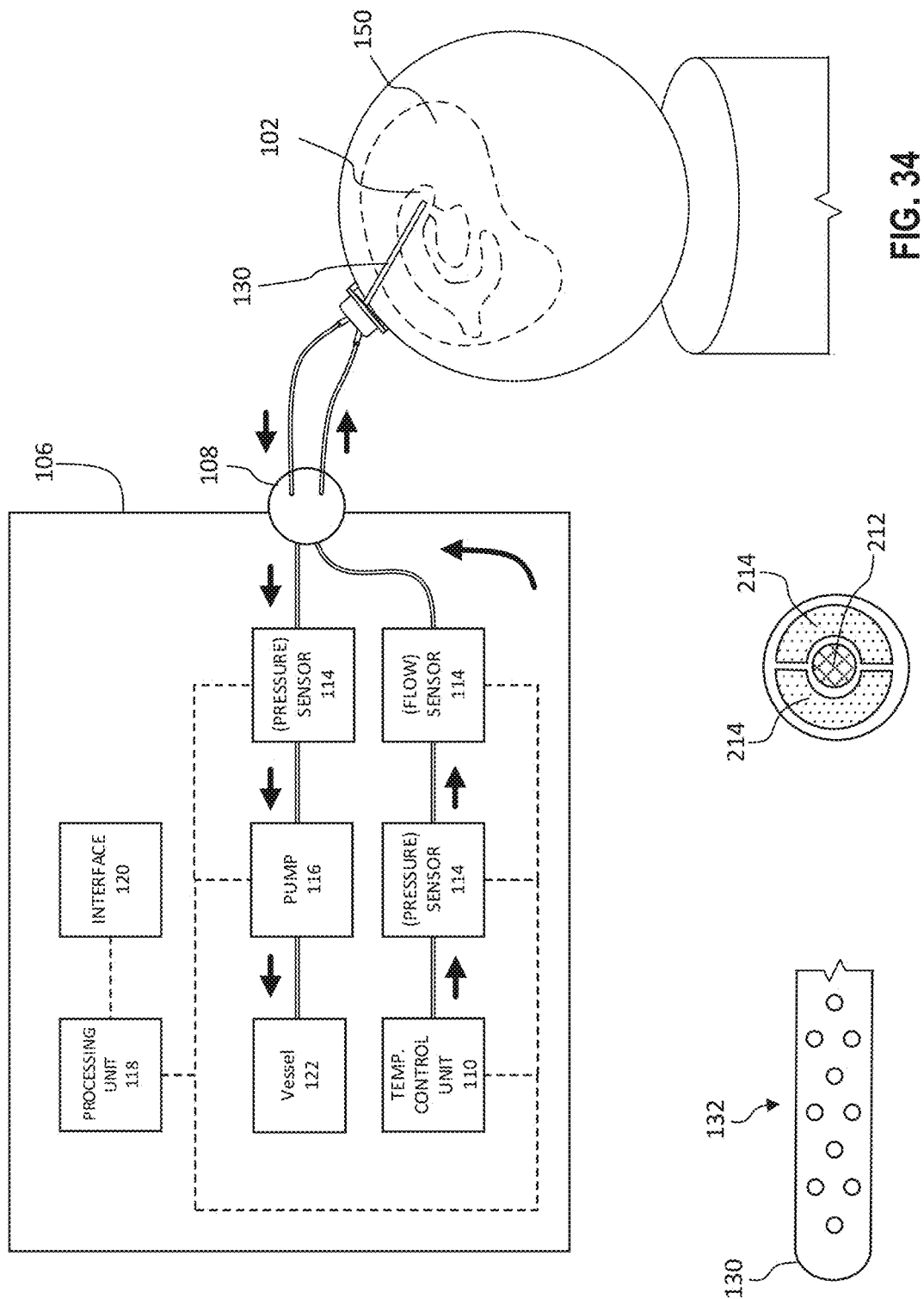

DEVICES AND METHODS FOR PROVIDING FOCAL COOLING TO THE BRAIN AND SPINAL CORD

CROSS-REFERENCE TO RELATED APPLICATIONS

This application is a non-provisional application of U.S. Provisional Application No. 62/237,867 entitled "Devices and Methods for Providing Focal Cooling to the Brain and Spinal Cord," filed Oct. 6, 2015, which is hereby incorporated by reference as if fully set forth herein.

Embodiments described in this application may be used in combination or conjunction, or otherwise, with the subject matter described in one or more of the following:

U.S. patent application Ser. No. 14/743,652, filed Jun. 18, 2015, entitled "Devices and Systems for Access and Navigation of Cerebrospinal Fluid Space";

U.S. patent application Ser. No. 13/801,215, filed Mar. 13, 2013, entitled "Cerebrospinal Fluid Purification System,"; and U.S. Provisional Application No. 62/201,287, filed Aug. 5, 2015, entitled "Tangential Flow Filter System for the Filtration of Materials from Biologic Fluids".

Each and every one of these documents is hereby incorporated by reference as if fully set forth herein.

BACKGROUND

Managing inflammation in neurocritical care is often desirable. There are a number of indications that could benefit from cooling, including spinal cord injury, traumatic brain injury, head trauma, cerebral ischemia, seizures, fever, thoraco-abdominal aortic aneurysms (TAAA), hydrocephalus, cerebrospinal fluid (CSF) leaks, aneurysmal subarachnoid hemorrhage, and others.

Fever occurs in 20-50% of critically ill neurologic patients and may adversely affect neurologic outcome. Specifically, fever occurs in up to 40% of patients with ischemic stroke and intracerebral hemorrhage and in 40-70% of patients with severe traumatic brain injury or aneurysmal subarachnoid hemorrhage. Fever is independently associated with increased morbidity and mortality after ischemic and hemorrhagic stroke. In subarachnoid hemorrhage and traumatic brain injury patients, temperature elevation has been linked with increased intracranial pressure.

Regarding spinal cord injury, although significant damage is caused by the mechanics of the traumatic spinal cord injury, secondary injury that follows is often even more dangerous. It occurs within the first 12-24 hours following the injury and can last up to 5-10 days, depending on the severity of the injury. Secondary injury causes physiological disturbances that disrupt the body's homeostasis, such as initiating a cellular inflammatory response at the injury site and increasing the release of free radicals. An overabundance of free radicals contributes to tissue ischemia, cerebral edema, and disruption of the spine-blood barrier. The use of hypothermia as a therapeutic agent has been shown effective in providing neuroprotection from secondary injury. Research has shown the benefits of hypothermia include decreasing oxygen consumption, free radical generation, neurotransmitter release, inflammation, and metabolic demands. Even a temperature decrease of 1-2° C. can be beneficial at the cellular level.

As disease awareness and diagnostic modalities continue to improve, the prevalence of thoracic and thoracoabdominal aortic aneurysm (TAAA and dissection) is increasing, affecting up to 16.3 individuals per 100,000 per year. Paraplegia remains one of the most devastating complications of thoracoabdominal aortic surgery, and is associated with a significant increase in both morbidity and mortality. Both pharmacological and mechanical modalities used to control central hypertension during aortic occlusion affect CSF dynamics and spinal cord perfusion pressure. Although lumbar drainage has been successfully used for TAAA patients for over 10 years, their introduction to TAAA as standard of care has been slow to evolve. In fact, lumbar drainage has cut the rate of paraplegia from 30% to 10-15% and the growth of minimally invasive TEVAR procedures has meant that the rate is now conservatively estimated at about 5-7%. This still means that approximately 15,500 people die or experience permanent weakness and disability each year. The two main approaches to protect the spinal cord during TAAA repair include maximizing spinal cord perfusion and inducting systemic hypothermia. Regional hypothermia may have fewer side effects, but epidural cooling can cause a sharp increase in CSF pressure and attenuate spinal cord perfusion.

Traumatic brain injury is a major source of death and severe disability worldwide. In the United States alone, 1.7 million people suffer a traumatic brain injury each year. Approximately 52,000 people die and 80,000 remain permanently disabled. Therapeutic hypothermia can be an effective intervention to reduce intracranial pressure and protect against secondary ischemic neuronal injury. Despite its therapeutic benefit, systemic hypothermia is associated with many potential side effects that have limited its widespread use including depth of cooling, coagulopathies, shivering, arrhythmias, and immune suppression, with increased susceptibility to infection and electrolyte imbalance. Furthermore, following a traumatic brain injury, a variety of inflammatory cytokines (e.g. IL-1, IL-6, and TNF) have been shown to worsen neuroinflammation, contribute to secondary brain damage and worse long-term outcomes.

Current methods for cooling include inducing systemic hypothermia in a patient, the use of cooling helmets, cooling the patient's blood, and circulating coolant through a closed loop within the CSF space. Typical ranges of systemic hypothermia include 32° C. to 34° C. There are several reasons why hypothermia is challenging to implement clinically despite its benefits. Current hypothermia methods can cause serious adverse events, such as arrhythmias, infection, sepsis, coagulopathy, electrolyte abnormalities, mild acidosis, a rise in lactate levels/amylase levels, excessive localized cooling or necrosis, skin issues, and other issues. Accordingly, there is a need in the art to provide cooling without the risks of current methods.

SUMMARY

Certain embodiments may provide focal cooling at a treatment site of a human or animal subject by deploying a multi-lumen catheter (i.e., a catheter with two or more lumens) near the treatment site. CSF may be withdrawn from near the treatment site through an inlet lumen of the catheter. The withdrawn CSF may be chilled and then returned through an outlet lumen of the catheter. A characteristic of the treatment site may be measured using a sensor and then compared against a treatment target. The comparison may then be used to modify a treatment parameter.

Certain embodiments may provide focal cooling at a treatment site of a human or animal subject by deploying a multi-lumen catheter near the treatment site. CSF may be withdrawn or drained from near the treatment site through an inlet lumen of the catheter. A heat transfer fluid may be circulated through a cooling lumen of the catheter. A characteristic of the treatment site may be measured by a sensor. The measured characteristic may be compared with a treatment target and used to modify a treatment parameter.

Certain embodiments may provide focal cooling at a treatment site of a subject by cooling the treatment site until a first treatment target is reached, maintaining a temperature at the treatment site until a second treatment target is reached, and enabling the treatment site to reach a third treatment target. As used herein, references to a "temperature" are understood to refer to a desired temperature range, as appropriate. The first treatment target may comprise a first temperature and a first period of time. The second treatment target may comprise a first temperature and a second period of time. The third treatment target comprising a third period of time and a second temperature that is higher than the first temperature.

BRIEF DESCRIPTION OF THE DRAWINGS

FIG. 8 illustrates a cross section of another embodiment of a catheter.

FIG. 9 illustrates an embodiment of a catheter, including a stylet.

FIG. 10 illustrates an embodiment of the catheter of FIG. 9, with the stylet removed.

FIG. 19 illustrates an embodiment of a method and system for withdrawing, treating, and returning CSF to a portion of a spine.

FIG. 20 illustrates portions of a catheter, including a first and second plurality of ports, of one embodiment of the invention.

FIG. 21 illustrates a cross section of a catheter of one embodiment of the invention.

FIG. 22 illustrates an embodiment of a method and system for withdrawing, treating, and returning CSF to a cerebral ventricle.

FIG. 23 illustrates a portion of a catheter, including a first and second plurality of ports, of one embodiment of the invention.

FIG. 24 illustrates a cross section of a catheter of one embodiment of the invention.

FIG. 25 illustrates an embodiment of a method and system for filtering CSF and cooling a portion of a spine.

FIG. 26 illustrates portions of a catheter, including a first and second plurality of ports, of one embodiment of the invention.

FIG. 27 illustrates a cross section of a catheter of one embodiment of the invention.

FIG. 28 illustrates an embodiment of a method and system for filtering CSF and cooling a cerebral ventricle.

FIG. 29 illustrates a portion of a catheter, including a first and second plurality of ports, of one embodiment of the invention.

FIG. 30 illustrates a cross section of a catheter of one embodiment of the invention.

FIG. 31 illustrates methods and systems for draining CSF from a portion of a spine and cooling a portion of the spine.

FIG. 32 illustrates portions of a catheter, including a first and second plurality of ports, of one embodiment of the invention.

FIG. 33 illustrates a cross section of a catheter of one embodiment of the invention.

FIG. 34 illustrates embodiments of systems and methods for draining CSF from a cerebral ventricle and cooling the cerebral ventricle.

FIG. 35 illustrates a portion of a catheter of one embodiment of the invention.

FIG. 36 illustrates a cross section of a catheter of one embodiment of the invention.

DETAILED DESCRIPTION

Figure 2:
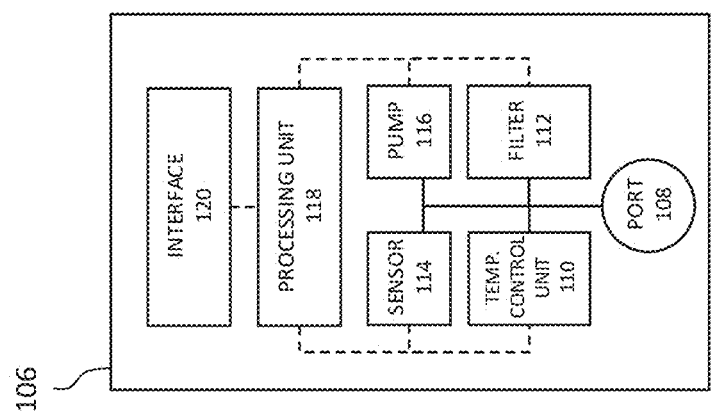
FIG. 2 illustrates a block diagram of a treatment unit according to certain embodiments.

Disclosed embodiments generally relate to systems and methods for focal cooling of the brain and spinal cord of a human or animal subject; however, applications may extend beyond focal cooling of these regions to other anatomical locations and other temperature modification (e.g., normothermia or focal warming). Some embodiments may provide selective spinal cord cooling, pressure monitoring and automated drainage. Such embodiments may include a multilumen catheter, a drainage collection reservoir bag, a pump to circulate fluid, sensor hardware and controllers. Embodiments may modulate the flow of the circulating fluid for cooling to modulate therapeutic hypothermia and re-warming. Embodiments may enable local hypothermic neuroprotection, limit the stress of cooling, minimize secondary neuronal damage and achieve neuroprotection while improving workflow as a result of automated drainage.

Disclosed focal cooling methods may enable cooling to about 30° C. or about 25° C., below safe ranges for present techniques, including for systemic hypothermia. In addition, focal spinal cooling may trigger a cascade of neuroprotective reactions that have an overall beneficial setpoint control effect. Accordingly, focalized cooling techniques disclosed here may be even more neuroprotective than traditional systemic hypothermic techniques. Cooling of 6° C. below normal internal human body temperature (approximately 37° C.) may benefit a patient and may amount to an approximately 50% decreased metabolic rate.

Another advantage is that the disclosed systems and methods allow for rapid cooling and rapid rewarming. Inflammation and temperature control occurs in the brain, so the focus on thermoregulatory centers versus indirect cooling in blood provides improved patient outcomes.

Disclosed embodiments may also be used to minimize inflammation in neurocritical care. In particular, cytokine filtration combined with drainage and cooling of CSF may provide a potent rapid therapy that improves outcomes in multiple disease states. Decreasing the cytotox load by approximately 50% and cooling the brain to between about 25° C. to 30° C. may be highly beneficial in severe manifestations of the aforementioned indications.

In certain embodiments, CSF is withdrawn from the spine, cooled, and returned. Certain embodiments may provide cooling using catheters with any suitable number of lumens, such as one or more single-lumen catheters inserted into the subject at one or more locations, a dual-lumen catheter, a tri-lumen catheter with a drainage lumen, or other catheter configurations. Certain embodiments may be configured with a set-it-and-forget-it configuration such that the CSF is withdrawn and temperature controlled using a feedback control system. Certain embodiments may take the form of a lumbar drain having a lumen to circulate a heat transfer fluid.

In certain embodiments, a catheter may be configured for use in cerebral ventricles. In addition, a ventricular cooling catheter that can cool and aspirate may provide benefits in sub arachnoid hemorrhage, fever control, seizure control, intracerebral hemorrhage evacuation, traumatic brain injury recovery, and other treatments. A ventricular catheter may enable cooling that is rapid, uniform, and targeted. Embodiments of catheters for use in the cerebral ventricles may be similar to or the same as catheters used in the spine.

Certain embodiments may be configured to take into account and overcome the natural warming of the brain and spinal cord by the body. The body typically produces approximately 400 to 500 mL of CSF per day. The system may be configured to treat any suitable amount of CSF per hour, such as approximately 120 mL of CSF per hour. The system may be configured to treat approximately 840 mL per hour. Warm blood (about 37° C.) may arrive at the brain at a rate of approximately 800 mL an hour. The treatment flow rate of CSF may be configured to match that rate. In certain embodiments, the flow rate of CSF may be configured to exceed that rate. For example, a flow rate of 900 to 1800 mL per hour may be used.

Embodiments may provide significant cost-saving workflows in intensive care units and operating rooms as a result of automation compared to gravity-based manual drainage systems. As a result of closed-loop sensing and control provided by some embodiments, intracranial pressure may be controlled using sensors to monitor and maintain a neuroprotective state. Cooling algorithms to maintain and modulate mild-moderate and deep localized hypothermia for up to 24 hours or more may be utilized.

General System

Figure 1:
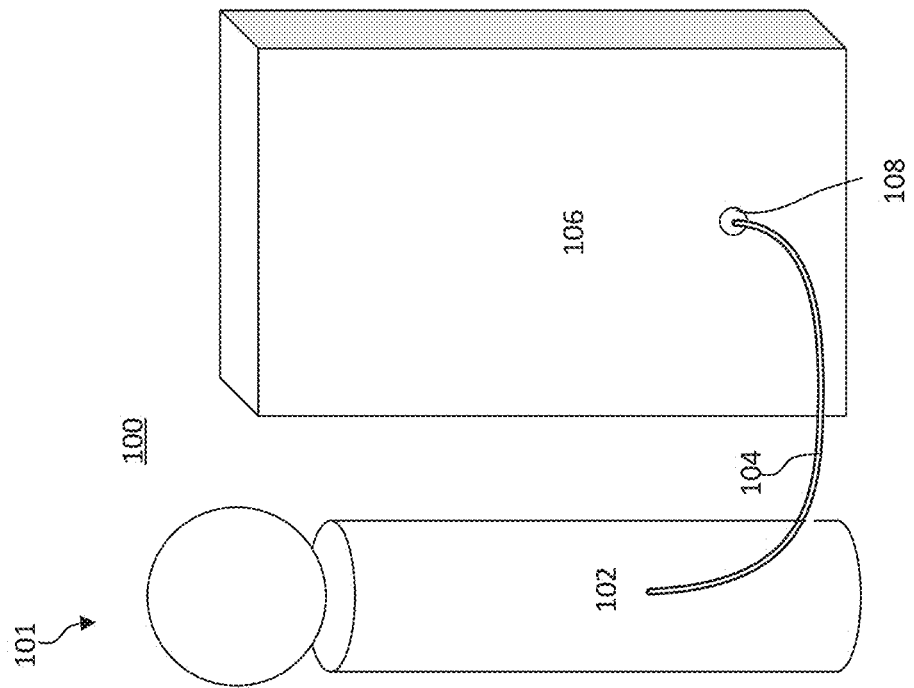
FIG. 1 illustrates a system for treating biological fluids or systems according to certain embodiments.

FIG. 1 illustrates an embodiment of a system 100 for treating biologic fluids or systems, including a subject 101, a treatment site 102, tubing 104, treatment unit 106, and port 108.

The subject 101 may be a human or animal subject undergoing treatment. The subject may have a treatment site 102. The treatment site 102 may be a location at or to which therapy is applied, but the treatment site 102 may, but need not be, the ultimate target of treatment. For example, in a particular treatment, the target tissue may be brain tissue, but it may be treated indirectly by cooling CSF introduced in the spinal region. As another example, brain tissue may be the treatment target and be treated by the application of a cooling balloon against brain tissue in cerebral ventricles of the subject 101. In certain embodiments, the treatment site 102 may be a CSF-containing space. The treatment site 102 may be a source of a fluid, a destination of a fluid (e.g., CSF), or both. For example, the system 100 may remove or receive a volume of fluid from the treatment site 102, perform cooling, filtration, and/or other treatment, and return a portion of the processed and/or treated fluid to the treatment site 102.

The connection between the system 100 and the treatment site 102 may be made in a variety of ways. For example, the connection with the treatment site 102 from system 100 may be made through one or more catheters inserted into particular anatomical locations. For example, the catheter may be a multi-lumen catheter inserted through a single opening in the subject to access the anatomical location, or may be two catheters inserted at different but connected anatomical locations.

The various components of the system 100 may be connected through tubing 104. For instance, in certain embodiments, there may be a length of the tubing 104 placing the treatment site 102 in fluid connection with the port 108. The tubing 104 may be any suitable material or system for transporting or containing fluid. While the connections of the system 100 are shown as being direct, the connections need not be. The various portions of the system 100 may be connected through combinations of connections and various tubing 104. In certain embodiments, the tubing 104 and other portions of the system 100 may be filled with priming fluid (e.g., saline). Longer lengths of tubing 104 may correspondingly comprise a larger amount of priming fluid; however, in certain implementations, larger amounts of priming fluid may result in an undesirable amount of dilution of "natural" fluid, such as CSF. Accordingly, in certain implementations, the tubing 104 may be selected in order to minimize the volume of priming fluid needed, while still having the system be practically useful (e.g., enough tubing to enable the system 100 to be used at a subject's bedside). Depending on the subject and the treatment site 102, the tolerance for removal or dilution of fluid may vary, and the system 100 may be scaled accordingly. For example, the parameters of the system 100 may be changed to scale to suit subjects ranging from a mouse to a human or larger mammals.

In certain embodiments, the tubing 104 may be insulated to decrease warming of fluid (e.g., heat transfer fluid and/or CSF) as it travels through the tubing 104. In certain embodiments, the tubing may be placed within an ice bath or other cooling source to cool the fluid in addition to or instead of using the temperature control unit 110 of the treatment unit 106. In certain embodiments, the tubing 104 may be comprise a jacket that surrounds the tubing 104. The jacket may be insulated to limit temperature changes in the fluid passing through the tubing. The jacket may also be configured to modify the temperature of the fluid. For example, the jacket may comprise coils through which warmed or cooled liquid may flow in order to modify the temperature of the tubing and the fluid flowing therein.

The treatment unit 106 may be a device or combination of devices configured to cool or otherwise treat fluid received through the port 108. The treatment unit 106 may be further configured in accordance with the disclosures herein (see, e.g., FIG. 2).

The port 108 may be a port through which fluid enters and exits the treatment unit 106. The port 108 may be any kind of port through which material or fluid may flow. The port 108 may be configured to be in fluid connection with the treatment site 102 using the tubing 104. The port 108 may include various fittings to facilitate the connection, including but not limited to compression fittings, flare fittings, bite fittings, quick connection fittings, Luer-type fittings, threaded fittings, and other components configured to enable fluid or other connection between two or more components. In addition to fittings, the port 108 may also include various elements to facilitate use of the system 100, including but not limited to various valves, flow regulators, adapters, converters, stopcocks, reducers, and other elements. In certain embodiments, there may be two or more ports 108. This configuration may facilitate the use of different systems with the treatment unit 106.

FIG. 2 illustrates a block diagram of a treatment unit 106, according to certain embodiments, with solid connections indicating example fluid flow connections for fluids and materials, and dashed connections indicating signal connections for the flow of signals and information. The treatment unit 106 may comprise the port 108, a temperature control unit 110, a filter 112, a sensor 114, a pump 116, a processing unit 118, and an interface 120.

The temperature control unit 110 may be a unit configured to cool fluid (or heat it, as needed to reach a desired temperature for the subject). Various techniques may be used depending on the fluid and the desired results, including but not limited to vapor-compression, thermoelectric cooling, radiator, other techniques, or combinations thereof. In certain embodiments, the fluid is CSF or other liquid removed from the subject 101 that will later be returned to the subject 101. In other embodiments, the fluid is a heat transfer fluid that may be circulated to cool the fluid or the treatment site. Certain embodiments may be configured to provide cooling for both biologic fluid and heat transfer fluid.

The filter 112 may be a device for separating a first portion of materials and/or fluid from a second portion of materials and/or fluid. The design and type of the filter 112 may vary depending on the type of fluid and the desired filtration results. Various kinds or combinations of filters may be used to achieve different kinds of filtration. For example, the filters may include filters of various pore sizes and different attributes, such as ultrafiltration, microfiltration, macrofiltration and other sized filters that have various porosities. Combinations of filters may include dead end filtration, depth filtration, tangential flow filtration, affinity filtration, centrifugal filtration, vacuum filtration, and/or combinations thereof. In an embodiment, the filter may be configured to filter cytokines. See U.S. Pat. No. 8,435,204, incorporated by reference herein for any and all purposes. Examples of cytokines and other proteins that may be filtered may include, but need to be limited to, EGF, Eotaxin, E-selectin, fas ligand, FGF2, Flt3 lig, fractalkine, G-CSF, GM-CSF, GRO, ICAM, IFNa2, IFNg, IL10, IL12p40, IL12p70, IL13, IL15, IL17, IL1a, IL1b, IL1ra, IL2, IL3, IL4, IL5, IL6, IL7, IL8, IL9, integrins, IP10, L-selectin, MCP1, MCP3, MDC, MIP1a, MIP1b, PDGF-AA, PDGF-AAAB, P-selectin, RANTES, sCD40L, sIL2R, TGFa, TNF, TNFb, VCAM, VEGF, and others. In some embodiments, the filter may be configured to capture and absorb cytokines in the about 10 to about 50 kDa range where most cytokines reside.

The sensor 114 may be a device for generating and/or receiving information. In certain embodiments, the sensor 114 may receive or generate information regarding characteristics of the fluid withdrawn from the treatment site 102, before, after, and/or during treatment. The characteristics may include, for example, temperature, pressure, the fluid flow rate to the treatment site 102, fluid flow rate from the treatment site 102, an amount of contaminants in the fluid, a type of contaminants in the fluid, other measurements of the fluid, and/or combinations thereof. The sensor 114 may be configured to generate or receive information regarding components of the system 100, such as a status of the temperature control unit 110, an efficiency rating of the temperature control unit 110, a status of the filter 112, an efficiency rating of the filter 112, a status of the pump 116, an efficiency rating of the pump 116, and an indication of clogs within the system. While the sensor 114 is shown within the treatment unit 106, one or more sensors 114 may be located elsewhere in the system 100 and/or cooperate with other locations. For example, the sensor 114 may include sensors configured to take readings from the subject 101. The sensor 114 may convert the data into computer- and/or human-readable representations for processing and review. While a single sensor is shown within the system 100, it will be understood that there need not be only as single sensor. Any suitable number of sensors may be used for taking one or more readings throughout the system.

In some embodiments, the sensor 114 may be selected to or optimized for use with flow rates of approximately 0 to approximately 1200 milliliters per hour, volumes of approximately 100 to approximately 125 cubic centimeters, and pressures of approximately 0 to approximately 20 mmHg. These measurement ranges may be encountered in the system, such as in the flow rate, volume, and pressure of CSF or a heat exchange fluid. In some embodiments, the flow sensor may be accurate within a range of between approximately 0 to approximately 2400 milliliters per hour, the pressure sensor may have an effective operating range of between approximately −50 mmHg and approximately 300 mmHg. In some embodiments, sensor 114 may have a response time of approximately 20 ms. In some embodiments, the sensor 114 may be a temperature sensor configured to have an accuracy of +/−0.5° C. between approximately 4° C. and approximately 70° C. Suitable sensors may include flow sensors provided by SENSIRION of Switzerland, pressure sensors by UTAH MEDICAL of Midvale, Utah, and temperature sensors by SCILOG of Madison, Wis.

The pump 116 may be any device for inducing fluid flow through one or more portions of the treatment unit 106. In certain embodiments, the pump 116 may be a peristaltic pump, which may reduce the need for sterilization of complex pump components; however, other types of pumps may be used. The operation of the pump 116 may be controlled by modifying the operating parameters of the pump 116. This may enable the flow rate, pressure, and/or other parameters of the pump 116 to be changed. The pump 116 may also be used to withdraw the fluid from and/or return fluid to the treatment site 102. In certain embodiments having multi-lumen catheters, there may be one pump per lumen.

The processing unit 118 may be a device configured to control the operation of the treatment unit 106, for example by sending signals to the temperature control unit 110, filter 112, sensor 114, and/or pump 116. In some embodiments, the signals are sent in response to input from the interface 120. In certain embodiments, the processing unit 118 may be processing information, such as data received from the sensor 114 and/or the interface 120, and making decisions based on the information. In certain embodiments, the processing unit 118 may itself make decisions based on the information. For example, the processing unit 118 may include a processor and memory for running instructions configured to receive input, make decisions, and provide output. The processing unit 118 may be further configured to receive and log data or results from the various sensors of the system 100.

The interface 120 may be a device or system of devices configured to receive input and/or provide output. In certain embodiments, the interface 120 is a keyboard, touchpad, subject monitoring device, and/or other device configured to receive input. For example, a healthcare professional may use the interface 120 to start or stop the system 100 and to modify system parameters, such as the absolute duration of the procedure, pump speed, and other parameters. The interface 120 may also include a display, speaker, or other device for sending user-detectable signals. In certain implementations, the interface 120 may comprise a network interface configured to send communications to other devices. For example, the interface 120 may enable the treatment unit 106 to communicate with other cooling systems, filtration systems, flow control devices, a server, and/or other devices.

The system 100 and/or the treatment unit 106 may comprise various flow regulators and sensors to facilitate or otherwise control flow of fluid throughout the system 100. The flow regulators may be devices configured to regulate one or more fluid flow characteristics of the system 100. These characteristics may include but are not limited to flow rate, direction, and pressure. The flow regulator may include various components or subsystems for controlling flow characteristics and may include pressure regulators, back-pressure regulators, sensors, and/or other devices. The flow regulators may be controllable by other components of the system (e.g., processing unit 118).

Figure 3:
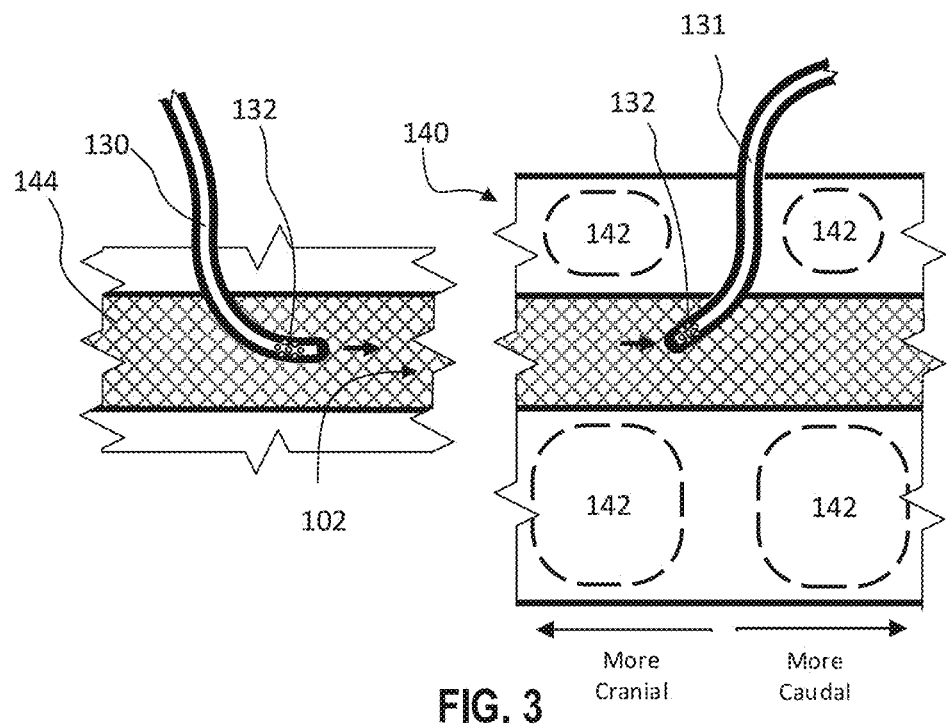
FIG. 3 illustrates a multi-catheter system for treating biological fluids or systems according to other embodiments of the present invention.

FIG. 3 illustrates a multi-catheter system for treating fluid near a treatment site 102. A first catheter 130 may be located at a first location and a second catheter 131 may be located at a second location. The first and second locations may be in fluid connection (e.g., two different portions of a CSF-containing space). A first catheter 130 may be deployed in a portion of a CSF-containing space that is more cranial than the location of the second catheter 131. For example, the first catheter 130 and the second catheter 131 may be inserted a distance of more than one vertebrae apart. In some embodiments, the first catheter 130 and/or ports 132 thereof may be located near or within the brain of the subject 101 (e.g., in a cerebral ventricle), in a lumbar region of the spine, in a cervical region of the spine, and/or in other suitable locations. As illustrated, the second catheter 131 is inserted into a CSF-containing space of a spinal portion 140, including vertebrae 142. As illustrated, the first catheter 130 has a plurality of ports 132 for returning the fluid 144, and the second catheter 131 has a plurality of ports 132 for withdrawing the fluid 144; however, their roles may be reversed even during treatment (e.g., the first catheter 130 withdraws the fluid 144 and the second catheter 131 returns the fluid 144).

While the catheters 130 are illustrated as entering in two different regions (e.g., through two different surgical sites), they need not be so configured. In some embodiments, two catheters 130, 131 may be inserted through a single surgical site and one of the catheters 130, 131 may be advanced a distance away from the other catheter 130. In addition, the catheters 130, 131 are illustrated as single-lumen catheters, but they need not be. The catheters 130, 131 may have multiple lumens. In addition, the catheters 130, 131 need not have ports 132. Instead, for example, the catheters 130, 131 may include a lumen for circulating heat transfer fluid in order to cool or warm the fluid 144 and/or the treatment site 102. While the catheters 130, 131 are illustrated as having a plurality of ports 132, there may be only a single port 132 in some embodiments. In addition, the ports 132 may be arranged in various configurations on or along the catheter 130.

Figure 4:
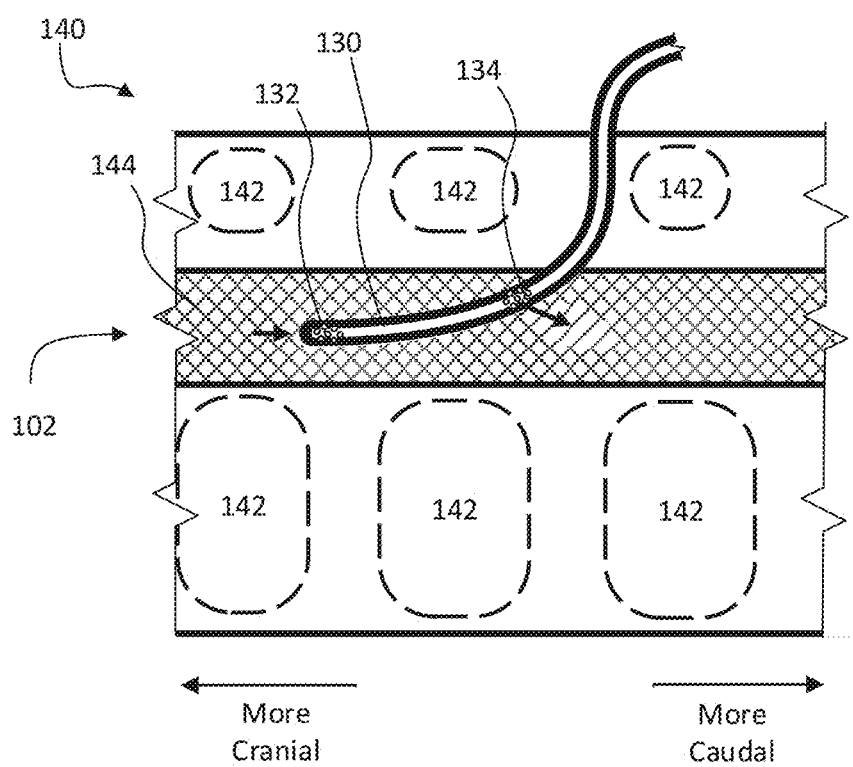
FIG. 4 illustrates an embodiment of a system for treating a portion of a spine.

FIG. 4 illustrates a system and method for treating fluid of a treatment site 102 in a spinal region 140, according to certain implementations. The certain implementations may include a portion of a spine 200 of the subject 101, including vertebrae 142, carrying a fluid 144 (for example, a fluid comprising CSF), and a multi-lumen catheter 130. The multi-lumen catheter 130 may comprise a first port or first plurality of ports 132 and a second port or second plurality of ports 134 that place the treatment site 102 in fluid connection with tubing 104. As illustrated, a first volume of the fluid 144 enters the multi-lumen catheter 130 through the first port 206 and is passed through into a portion of the tubing 104 (for example, a portion of tubing 104 leading to the port 108). A second volume of fluid 144 enters the multi-lumen catheter 130 from a portion of the tubing 104 and exits the multi-lumen catheter 130 through the second plurality of ports 134.

Figure 5:
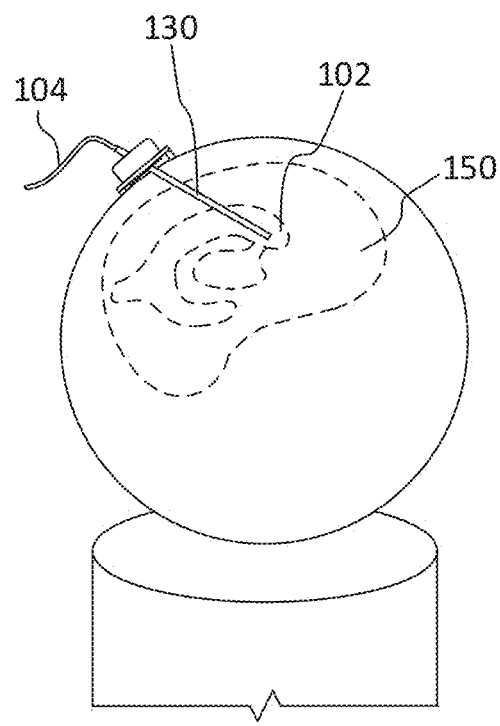
FIG. 5 illustrates an embodiment of a system for treating cerebral ventricles.

FIG. 5 illustrates a system and method for treating cerebral ventricles, according to certain implementations. In this particular example, the catheter 130 is placed in fluid connection with the ventricles of a subject's brain 210 in a configuration typically referred to as an external ventricular drain. In some examples, a system can be configured to cool more than one ventricle at a time, such as by placing a catheter in more than one ventricle or using multiple catheters for the ventricles. In certain implementations, the connection may be made via an external ventricular drain system. For example, the tip of a catheter may be placed in a lateral ventricle of the brain.

Although FIGS. 3-5 illustrate accessing CSF in a portion of the spine 200 or a portion of the brain 210, the embodiments disclosed herein need not be limited to those regions or that fluid. Embodiments may be used with other fluids, locations, or combinations of locations (e.g., a catheter located in a cerebral ventricle and another catheter located in a portion of the subarachnoid space). For example, one or more single-lumen catheters may be used to transport the fluid 144. Further, cooling need not be limited to one cooling circuit. For example, there can be more than one cooling circuit between the subarachnoid space and the ventricles. As another example, the anatomical location may be a blood vessel and the fluid may be blood.

Catheter Design

In certain embodiments, the catheter 130 may include one or more lumens. The catheter 130 may, but need not, also include ports to place one or more lumens in fluid connection with the fluid 144 of the treatment site 102. The catheter 130 may be generally configured to be flexible, navigable, and atraumatic. The catheter 130 may enable sensing of temperature, intracranial pressure, and/or other parameters. The size of the catheter 130 may be approximately greater than or equal to 6 French and approximately 20 to approximately 120 cm to enable attachment to remote tubing (e.g. the tubing 104), a console (e.g., the treatment unit 106), or other units; however, other sizes may be used. In some embodiments, the catheter size may be approximately 5 French.

Temperature control lumen. In certain embodiments, the catheter 130 may include a temperature control lumen. The temperature control lumen may be one or more lumens for circulating heat transfer fluid and be configured to cool fluid flowing through a different lumen of the catheter (e.g., an inlet or outlet lumen adjacent to the temperature control lumen), to modify the temperature of fluid flowing external to the catheter (e.g., CSF flowing through the treatment site 102), or a combination thereof. The temperature control lumens may contain multiple flow paths or channels to facilitate the circulation of heat transfer fluid within the temperature control lumen. In certain implementations, the temperature control lumen may extend substantially down the catheter 130 and then double back and return to facilitate the inflow and outflow of the heat transfer fluid. In certain embodiments, the heat transfer fluid may extend down the catheter and end in a dead end. The lumen may be scalloped or have structures to increase the surface area and increase or decrease temperature control ability. For example, the internal surface of the temperature control lumen may have internal fins, ridges, or other structures to encourage the exchange of heat from the heat transfer fluid to, for example, the fluid surrounding the catheter.

Inlet and outlet lumens. In certain embodiments, the catheter 130 may be configured with one or more inlet and/or outlet lumens. These lumens may be configured for the inflow and outflow of fluid 144 and, as such, may be in fluid connection with the fluid of the treatment site 102 through openings in the catheter 130. In certain embodiments, the catheter 130 need not have both inlet and outlet lumens. For example, a catheter maybe configured for draining fluid 144 only, and may have only an outlet lumen. As another example, a catheter configured only for adding fluid 144 may have only an inlet lumen.

Figure 6:
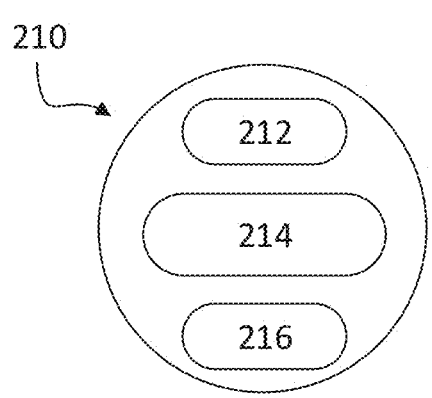
FIG. 6 illustrates a cross section of an embodiment of a catheter.

FIG. 6 illustrates a cross section of an example embodiment of a catheter 210 having an inlet lumen 212, a temperature control lumen 214, and an outlet lumen 216. As illustrated, the temperature control lumen 212 is disposed between the inlet lumen 212 and the outlet lumen 216. In addition, the temperature control lumen 214 may have a relatively larger surface area than the inlet lumen 212 and the outlet lumen 216.

Figure 7:
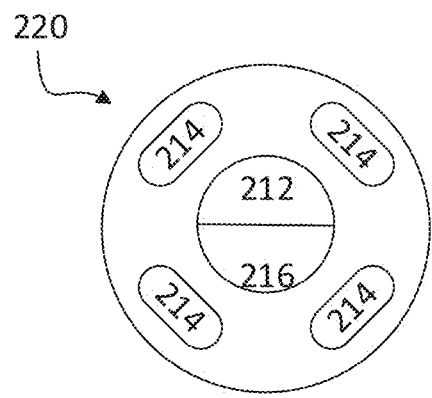
FIG. 7 illustrates a cross section of another embodiment of a catheter.

FIG. 7 illustrates a cross section of an example embodiment of a catheter 220 having an inlet lumen 212, four temperature control lumens 214, and an outlet lumen 216. The temperature control lumens 214 are located near the periphery of the catheter 220. These lumens 214 may be place in fluid connection with a balloon or other external features of the catheter 220.

FIGS. 8-10 illustrate an embodiment of a catheter 230 having a stylet to provide rigidity. FIG. 8 illustrates a cross section of the catheter 230, including temperature control lumens 234. FIG. 9 illustrates the catheter 230 with an inserted stylet 238. FIG. 10 illustrates the catheter 230 in a coiled configuration following the removal of the stylet 238. The catheter 230 may be constructed so as to form a substantially coiled, twisted, or otherwise distorted shape if a stylet 238 is not present within the catheter.

Increased surface area. In certain embodiments, the catheter may be configured to have an increased surface area to facilitate temperature control. The increased surface area may be created by the catheter having scalloped, bumpy, or otherwise inconsistent or complicated external shapes to provide additional surface area.

Heat transfer fluid. Various heat transfer fluids may be used, such as saline or perfluorocarbons. In certain embodiments, different heat transfer fluids may be used at different portions of the temperature control process. For example, the temperature control process may begin with saline as the primary heat transfer fluid and then, after a period of time, use of the saline is discontinued and perfluorocarbons and/or other materials are used. Alternatively, mixtures of fluids may be used, with such mixtures remaining constant and/or changing during the process.

Mixing elements. In certain embodiments, there may be elements or features of the catheter to facilitate mixing of the returning fluid in order to promote mixing of the cooled, returned fluid and the fluid still in the treatment site 102. The elements that enhance mixing can be external or internal to the body of the subject 101. In one example, the catheter 130 may include a helical or double helical design to create disruption and turbulence of passive CSF flow and more mixing and exchange of endogenous for processed CSF. Other examples include the creation of eddies or turbulence to enhance mixing through the use of jets or directed outflow. In other examples, small fins, nonplanar surfaces, ribbed portions, balloons, and/or other systems, such as along or within the length of the catheter 130, may promote mixing and/or exchange of endogenous and processed CSF.

Catheter materials. The catheter or portions thereof may be configured to utilize particular materials in order to encourage or discourage particular effects. For example, materials may be selected to encourage or discourage heat transfer to particular regions of the catheter. In particular, with reference to FIG. 7, there may be insulation disposed to limit cooling of the inlet lumen 212 by the temperature control lumens 214. This may be advantageous because the fluid in the inlet lumen 214 is leaving the body and cooling that fluid may have little effect on the temperature of the treatment site 102. Conversely, the outlet lumen 214 may lack insulation or be configured to encourage the fluid in the outlet lumen 214 to be cooled by the heat transfer fluid flowing through the temperature control lumen 214. Similarly, there may be materials to move the heat towards or away from an exterior of the catheter.

Infection mitigation. The catheter 130, tubing 104, and other portions of the system 100 may be configured to reduce the likelihood of infection or contamination of the treatment site 102. For example, the catheter's material may coated with protein-repellant coatings, microorganism-repellant coatings, antibiotic coatings, and/or coatings containing silver (e.g., silver nanoparticles) to discourage infection. As another example, protective sealants may be added to the brain. In some embodiments, anti-microbial components (e.g., washers) may be added to attachment points within the system in order to provide enhanced infection control.

Temperature Control Balloons

FIGS. 11-14 illustrate embodiments that include temperature control balloons. Temperature control balloons may be configured to be placed in contact with a wall of the lateral ventricle. The temperature control balloons may modify temperature by circulating heat transfer fluid in an expandable portion touching tissue near the treatment site 102 to cool the brain parenchyma, spinal cord, or other target. When utilized in a cerebral ventricle, the inflation of the balloon may displace CSF in the ventricles.

Figure 11:
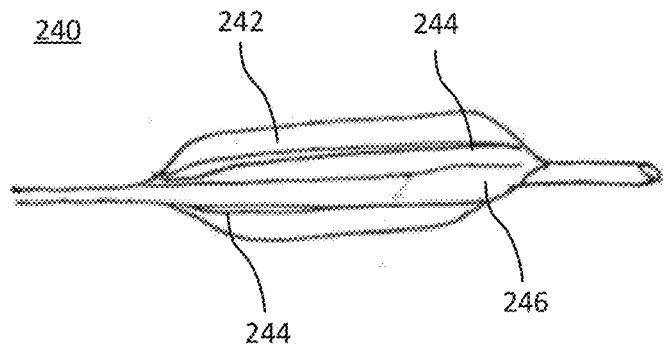
FIG. 11 illustrates an embodiment of a catheter having a cooling balloon.

FIG. 11 illustrates an embodiment of a catheter 240 having a temperature control balloon 242. Disposed in or on the balloon are pathways 244 through which heat transfer fluid may flow. The balloon may be expanded by filling it with air, fluid, or via other means. In addition to the pathways 244, there is a lumen 246 extending through the balloon. The lumen 246 may carry CSF, heat transfer fluid, or other fluid.

Figure 12:
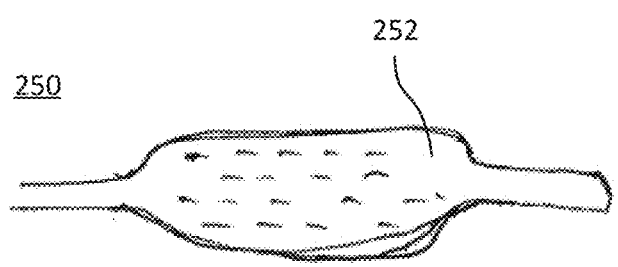
FIG. 12 illustrates another embodiment of a catheter having a cooling balloon.

FIG. 12 illustrates an embodiment of a catheter 250 having a temperature control balloon 252. The temperature control balloon is expanded by and filled with heat transfer fluid. Unlike catheter 240, this catheter 250 does not include an additional lumen 246.

Figure 13:
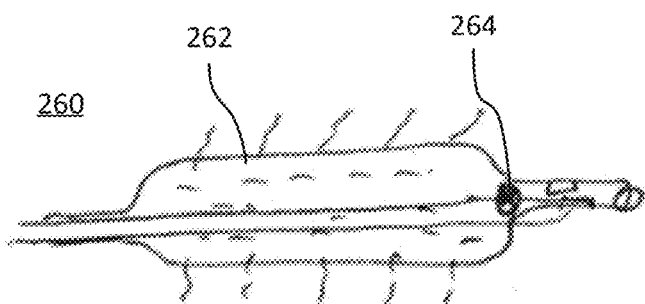
FIG. 13 illustrates another embodiment of a catheter having a cooling balloon.

FIG. 13 illustrates an embodiment of a catheter 260 having a temperature control balloon 262, a valve 264, and an additional lumen 266. Like the temperature control balloon 252 of catheter 250, the temperature control balloon 262 of catheter 260 is expanded by and filled with heat transfer fluid. When the balloon 252 is filled with heat transfer fluid, in addition to controlling the temperature (e.g., heating or cooling) materials adjacent to the outside of the balloon, the heat transfer fluid may change the temperature of fluid traveling through the additional lumen 266. The valve 264 may be configured to control the flow of heat transfer fluid through the catheter 260.

Figure 14:
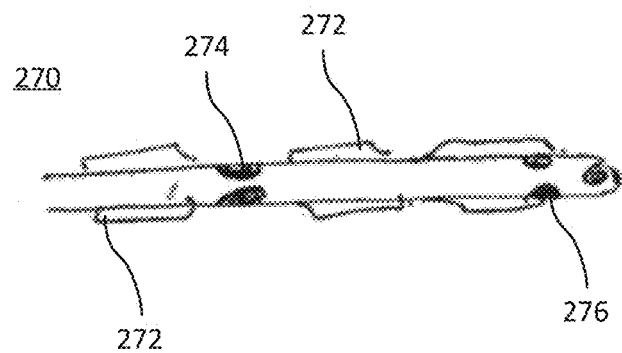
FIG. 14 illustrates an embodiment of a catheter having multiple cooling balloons.

FIG. 14 illustrates an embodiment of a catheter 270 including a plurality of balloons 272, an inlet 274, and an outlet 276.

Sensors

Various embodiments may comprise sensors for monitoring temperature, intracranial pressure, and other measurements.

Pressure sensors. In certain embodiments, a catheter may include pressure sensors positioned on, in, or about the catheter. The pressure sensors may be used to detect conditions in the overall flow circuit, and to detect blockages. A balloon may be positioned over the catheter and may be used to deploy flexible pressure sensors. In other embodiments, the flexible pressure sensors may be printed on a substrate (e.g., silicone).

Temperature sensors. A temperature sensor (e.g., fiber optic or thermocouple) may be used to sense a temperature or temperature gradient at a given point or series of points (e.g., at a treatment site 102, along a catheter, along tubing 104, in the system 100, or in other locations). A temperature sensor may be configured to collect a first reading in the spinal cord or in the brain parenchyma or in the tissue itself. There may be a tip sensor and a stepped algorithm such that for every interval of x seconds the temperature is checked. In another embodiment, a temperature sensor outside the body may read from a temperature sensor in the tissue as well as a temperature sensor in the CSF in the body and an algorithm may read temperature an interval of x seconds it checks the temperature. While there is a difference in temperature, the system may be configured to continue to cool or increase the flow rate of heat transfer fluid.

Surrogate volume measurements. In certain embodiments, it may be desirable to monitor the volume of fluid that has moved through the system 100. For example, embodiments controlling temperature based on controlling the flow of cooled CSF back into the system may be flow-rate dependent. In such embodiments, volume of cooled CSF returning to the system may need to be tracked in order to determine whether the cooled CSF overcomes the heat that that blood is bringing back to the brain.

In some embodiments, the rate at which the fluid is withdrawn from the treatment site 102 is between approximately 0.01 mL/min and approximately 100 mL/min. In some embodiments, the fluid rate may be approximately 0.1 mL/min to approximately 10 mL/min or approximately 8 mL/min to approximately 20 mL/min. Fluid may be returned at approximately the same rate as fluid is withdrawn, or it may be a different rate. However, the amount withdrawn or returned may be higher or lower depending on the application. The amount may vary depending on various factors including but not to the type of fluid being withdrawn, the viscosity of the fluid, the amount of fluid in the treatment site 102, and other factors. The viscosity of the fluid may vary over time, and depending on the particular subject 101. For example, the viscosity of CSF may be different in a subject 101 with meningitis than in a subject 101 who does not have meningitis.

As another example, during a surgery intracranial pressure may drop it may be desirable to determine the volume of fluid that had been removed. The volume removed may be measured in various direct and indirect ways. In certain embodiments, one or more flow meters may be used. For example, a flow meter may be placed to monitor the amount of fluid withdrawn from the treatment site 102. Another flow meter may be placed to monitor the amount of fluid returned to the treatment site 102. In implementations where fluid is stored by the system (e.g., in a bag), the volume of fluid in the bag may be measured to determine a volume withdrawn from the treatment site 102. For example, the bag may be weighed to determine the volume removed.

Cerebral blood flow measurements. In certain embodiments, the system 100 may also measure cerebral blood flow. For example, the Kety-Schmidt inert-gas technique, transcerebral double-indicator dilution technique, and/or other techniques may be used to measure the cerebral blood flow of the patient. The monitoring of cerebral blood flow may be used to sense and avoid vasoconstriction.

Electroencephalogram (EEG) monitoring. In certain implementations, the system 100 may include or cooperate with an EEG to read signals from the brain of the subject. In particular, there may be EEG electrodes or other sensors disposed on the catheter of the system. In addition to or instead of EEG electrodes on the catheter, there may be surface electrodes placed on the skin of the subject. The monitoring may be continuous or intermittent. The results of the EEG monitoring may be used to facilitate various outcomes, including but not limited to prediction and prognosis of brain activity and function following rewarming. EEG monitoring may also titrate therapy for seizure control.

Evoked potential monitoring. In certain implementations, the system 100 may be configured to receive evoked potential test results and/or conduct evoked potential tests. Evoked potential tests may measure electrical activity of the nervous system (e.g., portions of the spine) of the subject in response to stimulation of nerves. The evoked potential test results may be used to titrate the amount of cooling. For instance, the system may detect a 20% reduction in evoked potential and increase or decrease the temperature. The system may reduce the frequency of evoked potentials by a percentage and keep reducing the temperature until a minimum threshold (e.g. a temperature threshold or an evoked potential test result threshold) is reached.

Measuring intracranial pressure. The system 100 may be configured to read intracranial pressure and use the readings to modify therapy. In some embodiments, the intracranial pressure may be estimated based on a reading of intraocular pressure. In some embodiments, the system 100 may extrapolate thermomodulation, flow signatures, temperature readings, flow rate readings, and other parameters as a surrogate intracranial pressure. For example, a particular sensed flow rate reading may be extrapolated to determine whether there his high or low intracranial pressure.

Safety Systems

The systems and methods described herein may comprise various safety systems to promote the safe treatment of the subject 101.

Vasoconstriction avoidance module. For certain individuals, excessive cooling can result in vasoconstriction, which may cause headaches or other issues. Vasoconstriction may manifest itself as a change in pressure. Embodiments of disclosed systems may track pressure and incorporate it into a system-management algorithm. In particular, the algorithm may be configured to cause cooling until a pressure drop is detected (e.g., about 2-3 mmHg, about 5 mmHg, or other drops in pressure) and then hold cooling at that level.

Compartmentalization detection. In certain uses of temperature control systems, there may be a risk of compartmentalization within a CSF-carrying space. For example, in procedures addressing hydrocephalus, subarachnoid hemorrhage, stroke, or clots in the CSF-carrying space, it may be desirable to utilize a system having multiple pressure sensors to detect potential compartmentalization, By contrast, in certain uses, there may be less of a need for compartmentalization detection. For example, thoracic abdominal aneurysm procedures, it may be known that there is going to be good communication between different compartments of a brain or other CSF-carrying spaces.

In some embodiments, the system 100 may be configured to monitor the fluid flow rate and pressure at multiple points within the brain, other CSF-carrying spaces, and/or the catheter itself. If there is normal pressure hydrocephalus or other blockages, then there may be spikes in pressure and decreased flow as the catheter attempts to withdraw fluid and cannot. Depending on the measured pressure and/or flow rate, a gradient of values may result. Depending on where the low or high reading is located (e.g., at or near a particular pressure or flow sensor), the location of the problem may be triangulated. For example, the system may determine that the problem is located within a cervical, thoracic, or ventricular space.

Blockage detection and prevention. Certain embodiments may be configured to avoid, detect, and address potential blockages within the system. For example, in certain embodiments, the catheter may comprise multiple inlets and outlets to minimize the effect of clogs or blockages. The lumens of the catheter may include particular shapes to discourage clogging. For example, the lumens may combine various sizes, shapes (e.g., square, oval, and circular) to discourage clogging. Blockages may be detected through the monitoring of expected and actual flow rates, pressure, and other characteristics. For example, if a measured pressure is significantly higher or lower than expected, this reading may indicate a potential clog or blockage within the system.

Safety Mechanisms. The system may be configured to determine how and/or to what extent the subject is responding to therapy delivery. In some embodiments, the system may be configured to determine whether the subject is reacting adversely to therapy delivery. For example, the system may determine whether the subject is too cold, the subject is experiencing a spinal headache, or other adverse reactions. The system may also determine whether the subject is not reacting or not reacting enough to the therapy. In response to determine that the subject is reacting adversely or insufficiently to the therapy, the system may alter treatment parameters, such as duration of therapy or ramping of temperature or flow. Gradual ramping of temperature or flow rate can provided greater safety than causing rapid changes in temperature or flow rate. In some embodiments, the system may measure the subject's response to therapy based on readings of cardiovascular, nervous system, or other parameters or readings. The parameters and readings may include, but need not be limited to heart rate, blood pressure, blood oxygen level, EEG results, evoked potential, and/or other readings or combinations thereof.

Methods of Use—Extracorporeal Temperature Control, Generally

Figure 15:
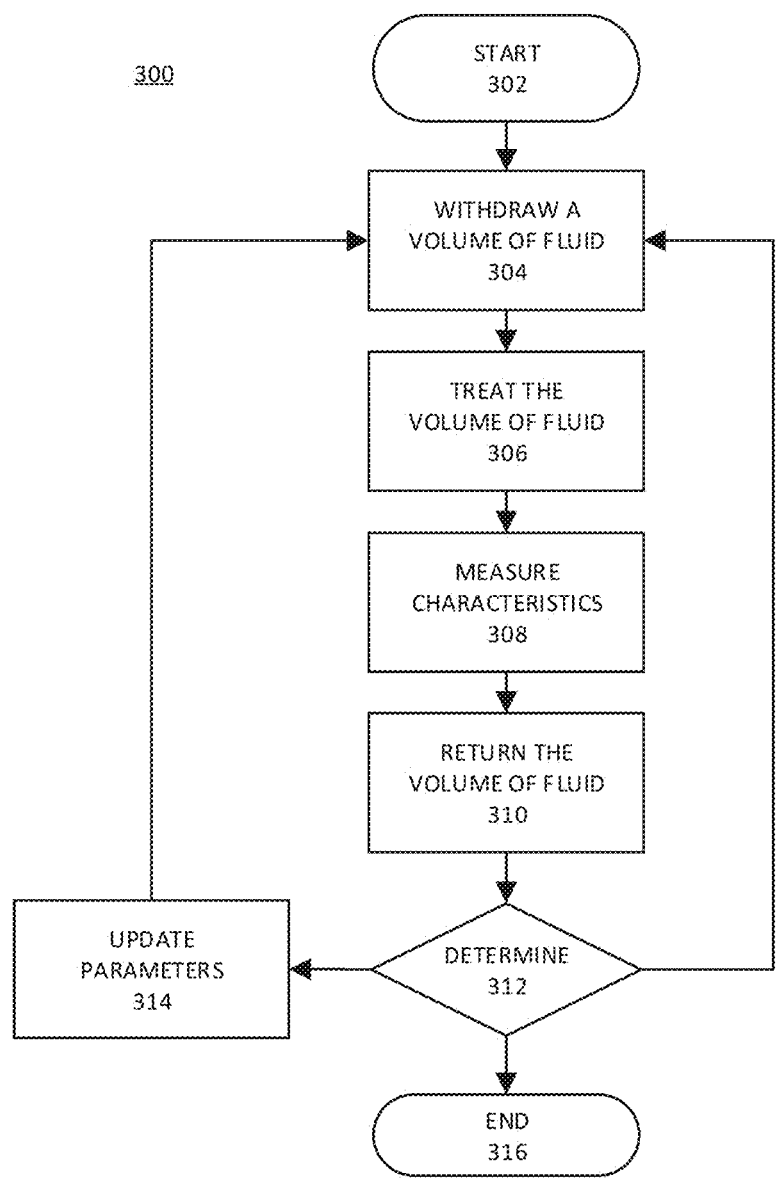
FIG. 15 illustrates a method for controlling extracorporeal treatment of fluid.

Extracorporeal temperature control. FIG. 15 illustrates a method 300 for using a treatment unit for the treatment of biologic fluids, including a starting step 302, a withdrawing a volume of fluid step 304, a treating the volume of fluid step 306, a measuring characteristics step 308, a returning the volume of fluid step 310, a determining step 312, an updating parameters step 314, and an ending step 316. The method 300 may be utilized with various embodiments, including system 100.

While the method 300 is described as being performed on a particular volume of fluid, the system may operate on a continuous flow of fluid. That is, the system 100 need not necessarily withdraw a volume of fluid, wait for the volume to be processed and returned, and then withdraw another volume of fluid. The method may follow a continuous process. Similarly, while FIG. 15 appears to illustrate a series of consecutive steps, the steps of the described method may occur concurrently. For example, the system 100 may concurrently perform some or all of the steps illustrated in FIG. 15. For instance, the system 100 may concurrently withdraw and return fluid.

The method 300 may begin at the starting step 302. This step 302 may include activating one or more components of the system 100. This step 302 may also include or follow various preparation steps. Such steps may include installing temperature control components, adding heat transfer fluid, installing filtration components, selecting and preparing the treatment site 102, installing tubing 104, calibrating components, priming components of the system, and other steps.

The selecting and preparing the treatment site 102 step may include choosing a particular treatment site 102. For example, a healthcare professional may select a subject 101 that may benefit from having treatment performed at a treatment site 102. Preparing the treatment site 102 may include identifying an anatomical location for a procedure to access the treatment site 102 (for example, in a spinal portion 142, as shown in FIG. 4), sterilizing the location, or otherwise preparing the treatment site 102 for the procedure. Selecting and preparing the treatment site 102 may be performed according to the systems and methods described within this application or through other means.

In some embodiments, preparing the treatment site may include placing an epidural needle into an introducer, accessing the subarachnoid space of the subject 101 using the needle and introducer, removing the needle while leaving the introducer in place, placing a guidewire, securing a catheter to the patient using a fixation device, peeling away the introducer, connecting the treatment system 100 to the catheter, and implanting the catheter using over-the-wire placement techniques. During the preparation, fluoroscopy may be used to verify access to the subarachnoid space, verify placement of the guidewire, and confirm placement of the catheter.

Installing tubing 104 may include connecting various components of the system 100. This step may include installing tubing 104 and the catheter 130 to the treatment site 102. This step may include inserting a multi-lumen catheter into an anatomical location to place the treatment site 102 in fluid connection with the system 100 to enable fluid to be drawn into the port 108 and returned to the treatment site 102.

Calibrating components may include setting initial parameters for the use of the system 100. This step may include establishing an initial flow rate, an initial temperature control rate, an initial pressure, and other initial parameters or system settings. The initial parameters may be based on observed or predicted clinical measures, including but not limited to an estimated amount of fluid in the treatment site 102, the health of the subject, the predicted ratio of retentate to permeate, and other factors.

Priming the system 100 may include adding a priming solution to one or more of the components of the system 100. Depending on the configuration of the system 100, priming may be necessary for one or more components to function effectively. Depending on the treatment site 102, fluid, and the subject, one or more components may be primed to improve comfort and health of the subject. In certain applications, the system 100 may be primed to enable the return of a volume of fluid while simultaneously withdrawing a volume of fluid. This may be especially useful for applications where the treatment site 102 has a relatively small volume of fluid (e.g., CSF) or is otherwise sensitive to relative changes in volume. Depending on the type of treatment, the length of the procedure, and other factors, priming fluid may be added during the filtration procedure to make up for fluid lost or used during the procedure.

At step 304, a volume of fluid is withdrawn from the treatment site 102. In certain circumstances, the fluid may be withdrawn using a pump or device located within the system 100 (e.g., pump 116). The pump may be used to withdraw a volume of fluid from the treatment site 102. Once the fluid is withdrawn from the treatment site 102, the fluid may pass through the tubing 104 and into the filtration system 102 via port 108.

At step 306, the volume of fluid is treated. The treatment of the fluid may include temperature control (e.g. using temperature control unit 110), warming (or allowing the fluid to warm), filtering (e.g., using filter 112), other treatment techniques, and/or combinations thereof. In certain embodiments, the fluid may be successively or progressively treated, such as by being cooled and/or filtered again through another process, system, or unit.

In certain embodiments, the rate of temperature control or warming may be altered by changing the heat transfer fluid used (e.g., changing from a heat transfer fluid having a high specific heat capacity to a heat transfer fluid having a low specific heat capacity). For example, if the heat transfer fluid is saline, it may be replaced with perfluorocarbon to achieve a different rate of temperature control. In particular, there may be an embodiment using saline as a heat transfer fluid and after a particular amount of time (e.g., three cycles of checking sensors) if the measured temperature has not changed by a significant amount (e.g., 1° C.), then the saline may be removed from the system and replaced with a different heat transfer fluid (e.g., a perflurocarbon) to attempt to change the temperature.

There are various means for rewarming fluid. In certain embodiments, the flow rate of heat transfer fluid may be reduced (e.g., the flowrate may be reduced from about 30 mL per minute to about 15 mL per minute to about 5 mL per minute), or the amount of heat transfer fluid used may be reduced. Other means may be used as well.

At step 308, characteristics of the subject 101, the treatment site 102, the fluid, and/or the system may be measured. Measuring characteristics may include intermittent or continuous sampling and/or monitoring of characteristics or parameters of interest. While this step 308 is shown as occurring after the filtration of the fluid 306, the step 308 may take place at any point during the process 300 where useful data may be gathered.

In certain embodiments, measuring characteristics may include measuring the characteristics of the fluid withdrawn from the treatment site 102 before, during, or after treatment. The characteristics measured may include the presence or amount of particular contaminants, proteins, compounds, markers, and other fluid components present. As another example, the ratio of permeate volume to retentate volume, the fluid flow rate from the treatment site 102, fluid temperature, fluid opacity or translucency or transparency, an absolute retentate flow rate, and the rate of fluid flow to the treatment site 102 also may be measured. The performance characteristics of the system 100 may also be measured. For example, the efficiency of the filter 112, the status of the filter 112 (for example, via the interface 210), and other markers of system 100 performance may be measured.

In certain embodiments, the characteristics measured may include information about a subject or input by a healthcare provider. For example, the system 100 may monitor the blood pressure, heart rate, stress, and other information of the subject. In addition to quantitative characteristics, qualitative measurements may be made as well. For instance, subject discomfort and other qualities may be measured. These and other data may be measured by the sensor 224 and/or be input into the system by an input device (for example, keyboard, touch screen, subject-monitoring device, and other devices for receiving input) operably coupled to the system 100.

At step 310, a volume of fluid is returned to the treatment site 102. In certain embodiments, the fluid is returned to the treatment site 102 as soon as fluid filtration has been completed. In certain embodiments, the flow rate of the fluid may be controlled. For example, a volume of fluid may be buffered in an area of the system 100 for a time before being returned to the treatment site 102. Buffering may be used to smooth the return rate of the fluid, to allow time for the fluid to reach a particular temperature, to allow time for a particular additive to mix within the fluid, and for other reasons.

In certain embodiments, the rate and/or pressure at which the fluid is returned to the treatment site 102 is controlled (for example, by a flow regulator). For example, the return of fluid is controlled so that the fluid is returned at such a rate or in such a manner as to maintain homeostasis within the treatment site 102. In certain embodiments, this may be accomplished by returning fluid at the same rate at which fluid is currently being withdrawn from the system. In certain embodiments, the fluid may be returned at substantially the same flow rate at which it was removed. The fluid volume removed from the system and returned to the system may not be equal. This may be the case when removing a significant quantity of contaminants from a treatment site 102. In certain embodiments, the difference may be made up through the addition of additional fluid.

In certain embodiments, a particular volume of additional fluid may be returned to the treatment site 102. The additional fluid may be fluid that was not withdrawn from the treatment site 102, previously withdrawn from the treatment site 102, withdrawn from a different treatment site 102, synthetically created, mixtures of these, or otherwise different from the volume removed from the treatment site 102 in step 304. The return of additional fluid may be used to, for example, compensate for a volume of fluid that was filtered out, especially in circumstances where the treatment site 102 comprised only a small amount of fluid at the start 402.

In certain embodiments, one or more therapeutic agents may be added to the fluid prior to its return to the treatment site 102. The fluid may be treated or mixed with a particular pharmacological agent. For example, when the fluid is CSF, the agent may be configured to bypass the blood-brain barrier. The agents may include, but need not be limited to, antibiotics, nerve growth factor, anti-inflammatory agents, pain-relief agents, agents designed to be delivered using intrathecal means, agents designed to affect a particular condition (e.g., meningitis, Alzheimer's disease, depression, chronic pain, and other conditions), and other agents.

As a specific example, the treatment site 102 may be a CSF-containing space of a subject, such as the subarachnoid space or another space known or thought to contain CSF. The space may only have a total of approximately 125 ml of CSF, and if the level drops below a certain threshold (for example, approximately 85 ml), the subject may suffer undesirable side effects. If a particular large amount of the existing CSF comprises undesirable compounds, the volume of permeate may be small enough to cause the fluid levels in the treatment site 102 to drop below the threshold. Consequently, the system 100 may return a volume of additional fluid (for example, artificial CSF or other suitable fluid) to adjust for the difference between the amount of withdrawn CSF being returned and the amount needed to be returned in order to maintain the volume of the treatment site 102 above the threshold amount.

In certain embodiments, the withdrawal and return of the fluid may occur in a pulsed manner. For example, the system 100 may withdraw a particular volume and then cease withdrawing additional fluid. The withdrawn volume is processed by the filtration or other systems and buffered (for example, at the combiner 116). Filtered amount from the buffer may be returned to the treatment site 102 at about the same rate and/or for the about same total volume as a next volume is withdrawn from the treatment site 102. This process may allow the system to maintain treatment site 102 volume levels relatively consistent and may be useful in circumstances where the processing time (for example, the time between the fluid being withdrawn from and returned to the treatment site 102) is long.

At step 312, a determination is made. The determination may be made by, for example, a healthcare professional, a processor system, or a combination thereof. For example, the healthcare professional may analyze the measured characteristics and come to a conclusion. As another example, the processing unit 118 may analyze the measured characteristics using an algorithm or through other mechanisms. The determination may be based on the measured parameters, a timer, a schedule, or other mechanisms. The determination may be used in order to change the parameters of the system 100 over time and to address particular measured characteristics.

For example, a determination may be made regarding the rate of cooling and/or warming of the treatment site. For example, based on the measured characteristics, the rate of temperature control may be too low or too high based on a target treatment time or treatment rate.

As another example, a determination may be made regarding the flow rate at which the fluid is being withdrawn and/or returned to the treatment site 102. For example, it may be desirable to maintain substantially the same withdrawal and return rate of the fluid. Specifically, if more fluid is being withdrawn from the treatment site 102 than is being returned, then the volume of fluid in the treatment site 102 may be decreasing overall. This may be undesirable because for certain fluids and certain treatment sites 102, if the volume of the treatment site 102 passes a particular threshold, undesirable side effects may occur. For instance, where the fluid being withdrawn is CSF, the flow rate may be such that the volume of CSF removed from a human subject does not exceed about between approximately 5 mL and approximately 20 mL over the course of one hour. That is, the volume of fluid does not decrease more than approximately 5 mL to approximately 20 mL from its original starting volume in a one hour period of time. In certain embodiments, it may be desirable to maintain an absolute retentate flow rate within a certain range of acceptable retentate flow rates. In certain embodiments, the threshold may be between approximately 0.10 mL/min and approximately 0.30 mL/min. In certain embodiments, the threshold may be approximately 0.16 mL/min. In certain embodiments, the threshold may be between approximately 0.2 mL/min and approximately 0.25 mL/min; however, other values may be desirable in certain circumstances.

Based on the measured characteristics, it may be determined that the best way to address the disparity in the withdrawal and return rates may be to decrease the flow rate to reduce the overall volume of fluid lost from the system. This may mean that, although there is a net loss of fluid from the treatment site 102, the loss is occurring at a slower rate. The rate may be sufficiently slow that, for example, that the subject's body produces sufficient fluid to make up for the loss.

As another example, the measured characteristics may be a subject's expressed discomfort. Withdrawing CSF from a CSF-containing space of a subject may cause symptoms of overdrainage, such as spinal headache. Symptoms of overdrainage may be able to be avoided or otherwise addressed by not withdrawing more than a threshold amount of CSF. However, the particular threshold may vary from subject to subject. As such, a predicted threshold may be different from an actual threshold and the subject may experience symptoms sooner than expected. In response to the subject expressing feelings of discomfort, the healthcare professional may determine that the parameters of the process may need to be changed.

In certain embodiments, at step 312, the processing unit 118 and/or a healthcare professional may determine that the process should be completed. At this point, the flow moves to end step 316. In certain other embodiments, at step 312, the processing unit 118 and/or a healthcare professional may determine that the process should continue substantially unchanged. Upon that determination, the flow diagram may return to step 304. In still other embodiments, at step 312, the processing unit 118 and/or a healthcare professional may determine that the one or more parameters of the process should be changed. Upon that determination, the flow diagram may move to step 314.

At step 314, one or more parameters of the system 100 are changed in response to a determination made in step 312. The parameters to be changed may include inflow rate, outflow rate, temperature control amount, and other parameters. Such parameters may be changed via, for example, the processing unit 118 sending a signal to the pump 116 or other component of the system in order to modify the parameters. In certain embodiments, the parameters may be manually changed through input received at the port 108. This may include parameters entered by a healthcare professional. In certain embodiments, parameters may be updated based on the difference between the withdrawal volume and the returned volume (e.g., a waste rate), a target temperature control rate and an actual temperature control rate, and other goals.

In certain embodiments, the updating parameters step 314 may include changing the flow direction of the fluid. For example, a system may include a plurality of treatment systems, which the fluid may be directed to by the manipulation of a valve or other mechanisms for changing fluid flow direction. Step 314 may include changing the fluid flow from one treatment system to a different treatment system. This may be in response to determining that a second treatment system is more suited for filtering particular contaminants than a first filtration system, for example.

In certain embodiments, the updating parameters step 314 may include modifying the positioning of the tubing at the treatment site 102. For example, one or more inflow or outflow tubes 114 may become clogged or otherwise be operate at a reduced capacity. In response, the tubing 104 may be adjusted or otherwise modified to address the reduced capacity issue. The healthcare professional may be alerted to the issue by a light, alarm or other indicia.

In certain embodiments, the updating parameters step 314 may include cleaning or otherwise modifying one or more components of the system 100, such as the filter 112. This may be accomplished by, for example, changing back pressure and pump speed.

In certain embodiments, the updating parameters step 314 may include sensing characteristics of the system to determine whether the filter 112 or other components of the system are experiencing clogging. The sensed characteristic may include reading an alert state of the filtration system or detecting an increase in filter pressure with no change to system flow rates or other parameters of the system. Responsive to determining that there may be a clog in the system 100, the flow rate through the retentate port of the filters may be increased. The increased flow rate may be the result of a user or the system opening a back pressure valve (e.g., a backpressure valve of a flow regulator). The opening of the valve may result in a surge of fluid through one or more retentate ports of one or more filters into a waste collection area. The surge of fluid may result in the flow returning to the treatment site 102 reducing to zero or even a negative rate. Thus, the operator or system controlling the flow rate may take into account the volume of fluid lost and the possible effects on the patient as a result of this filter clearance mechanism.

At step 316, the process comes to an end. After the process is completed, various wind-up steps may be performed, including but not limited to, applying a bandage to the subject, disassembling one or more components of the system 100, analyzing an amount of the withdrawn fluid, analyzing the retentate, and other steps.

Methods of Use—Direct Temperature Control at the Treatment Site, Generally.

Figure 16:
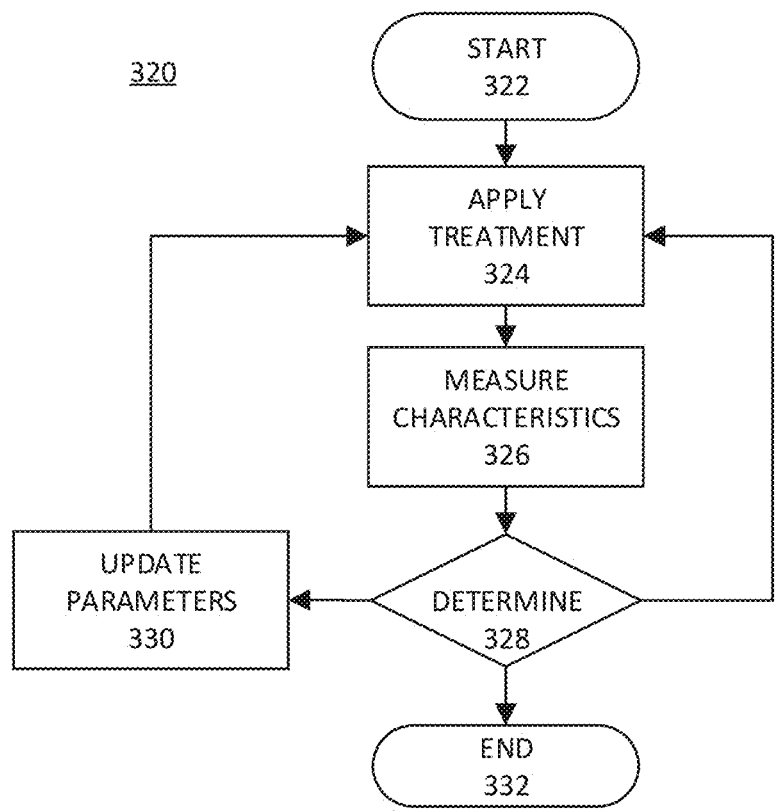
FIG. 16 illustrates a method for treating within a subject.

Temperature control in the treatment site. FIG. 16 illustrates a method 320 for temperature control at a treatment site 102. In particular, the method 320 may be a modified version of the method 300 of FIG. 15 directed toward direct temperature control at the treatment site 102. The method 320 may comprise a starting step 322, an applying treatment step 324, a measuring characteristics step 326, a determining step 328, an updating parameters step 330, and an ending step 322. The method may be utilized with certain embodiments, including system 100.

The starting step 322 may be substantially similar to step 302 of the method 300 and focused on temperature control directly within the treatment site 102. In particular, this step 322 may include inserting a catheter 130 into a treatment site, the catheter 130 having at least one temperature control lumen configured for the circulation of heat transfer fluid. This step 322 may also include preparing the treatment unit 106 for the temperature control and circulation of the heat transfer fluid within the catheter 130.

The applying treatment step 324 may include causing the temperature control, causing the warming, or otherwise treating the treatment site 102. This may include, but need not be limited to, circulating a heat transfer fluid within a temperature control lumen of the catheter 130. The heat transfer fluid may be cooled and/or warmed by the temperature control unit 110. The heat transfer fluid may circulate at a particular rate, temperature, volume, and other characteristics. These characteristics may be modifiable at the temperature control unit 110.

The measuring characteristics step 326 may include measuring characteristics of the heat transfer fluid, treatment site, and/or other portions of the system. This step 326 may be similar to the step 308 of the method 300.

The determining step 328 may include determining how to proceed with treatment of the treatment site 102. This step may be similar to the determinations made in step 312 of method 300. For example, the determining step 328 may include determining how the measured characteristics compare with desired goals and targets for treatment. In particular, the current rate of temperature control may be compared with a desired or target rate of temperature control. The determination may be made that particular parameters of the treatment may need to be changed in order to reach a desired clinical or other outcome. If a determination is made that one or more parameters of the system 100 needs to or should be changed, the flow of the diagram may move to the update parameters step 330. If a determination is made that treatment should end, then the flow may move to the ending step 332.

The update parameters step 330 may include modifying one or more parameters of the system 100 based on the determining step 328. The update parameters step 330 may be similar to the update parameters step 314. This step 330 may include changing the temperature of the heat transfer fluid, the flow rate of the heat transfer fluid, the type of heat transfer fluid, and/or other parameters of the treatment to more closely track a desired treatment target.

At step 332, the process comes to an end. After the process is completed, various wind-up steps may be performed, including but not limited to, applying a bandage to the subject, disassembling one or more components of the system 100, analyzing the results of treatment, and/or other steps.

Methods of Use—Particular Temperature Control Methods and Algorithms

Figure 17:
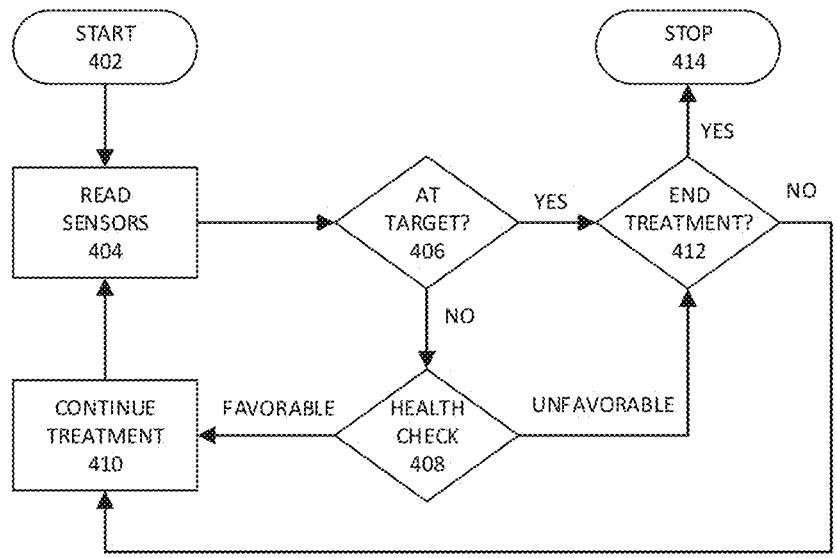
FIG. 17 illustrates an embodiment of a method for controlling treatment.
Figure 18:
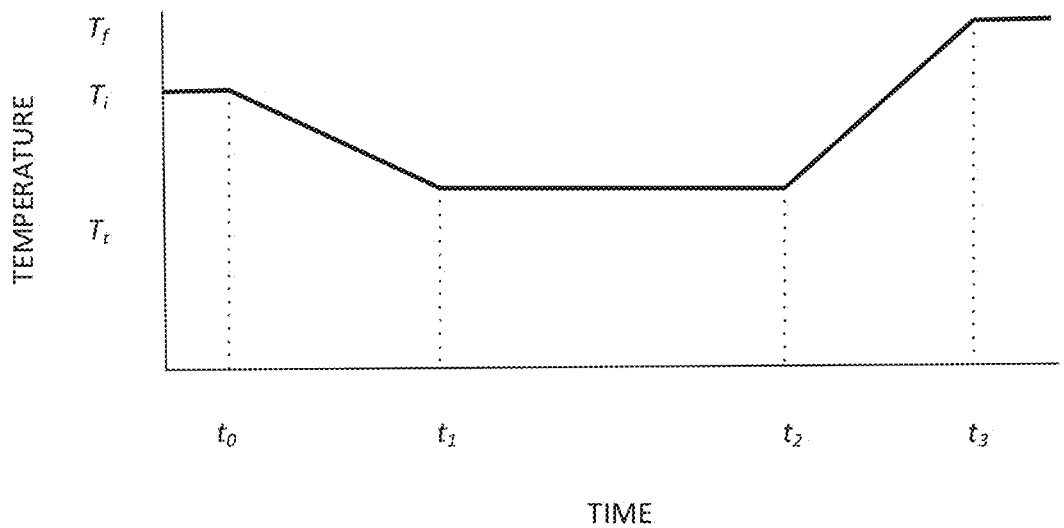
FIG. 18 illustrates an embodiment of a target treatment pattern for cooling CSF.

FIGS. 17 and 18 illustrate example methods for controlling treatment and updating parameters. In particular, FIG. 17 illustrates an example method 400 for controlling temperature. The method for controlling temperature may be used in conjunction with or instead of the methods described in FIGS. 15 and 16. The method may include a starting treatment step 402, a reading sensors step 404, a determining if a target is reached step 406, a performing a health check step 408, a continuing treatment step 410, a determining whether to end treatment step 412, and a stopping treatment step 414.

The method 400 begins at the start treatment step 402. The method 400 may start after various preparatory steps have been performed. In particular, a temperature control and sensing system may be configured to cool a fluid and read sensors. For example, a temperature control catheter may be inserted into a CSF-containing space of a subject's spine, and/or into one or more cerebral ventricles of the subject. The system may be configured to cool the fluid within the subject (e.g., by circulating heat transfer fluid through the catheter) and/or withdraw the fluid, cool the withdrawn fluid, and return the fluid.

The reading sensors step 404 may comprise reading sensor information from various sensors. The sensors may be temperature sensors, EEG sensors, intracranial pressure sensors, flow rate sensors, and/or other sensors for reading information pertaining to the subject, the fluid, or other sources. In certain embodiments, reading sensors may comprise measuring a functional biomarker (e.g., intracranial pressure, tissue temperature, and cytokine markers). In some embodiments, one or more sensors (e.g., pressure within the catheter or temperature) can be located on or within a catheter, such as at the tip of the catheter. Sensor information may be used in order to make decisions as to whether to increase, decrease, alter, or maintain a treatment.

The determining if a target is reached step 406 may include using the information received from step 404 to determine whether a target is reached. For example, the target may be a target temperature, a target flow rate, a target pressure, a target time, other targets, or a combination thereof. A target may be reached if the measured value meets, exceeds, passes, or falls within a particular range of a target value. If the target is reached, then the flow may move to the determining whether to end treatment step 412. If the target is not reached, then the flow may move to the performing a health check step 408. In addition, following this step 406, the target may be modified. A treatment of a subject may include one or more targets. If there are a plurality of targets, then there may be dependencies between targets (e.g., a first or a second target must be reached before moving to a third target).

In some embodiments, determining whether a target is reached may be as simple as determining whether the system is set to a target mode or has changed a target mode. For example, if the system was in a cooling mode and then the system detects a change to a maintain mode, then the method may move to the determining whether to end treatment step 412.

The performing a health check step 408 may include checking the health of the subject. The check may be performed using information read from the sensors in step 404, additional information gathered for this step 408, input from a health professional (e.g., observations made by a doctor), input from the subject (e.g., expressed discomfort), other sources, or combinations thereof. The check may result in a favorable or unfavorable health determination. For instance, an unfavorable health check may be the result of expressed discomfort by the patient, a core body temperature that is dangerously low, abnormal heart rate, abnormal heart rhythm, abnormal EEG results, abnormal intracranial pressure, sensor readings outside of expected ranges, other indications of an unfavorable health state in the patient, or combinations thereof. A favorable health check may be the result of a lack of unfavorable health determinations, sensed values in expected ranges, other indications of a favorable subject health state, or a combination thereof. If the health check is unfavorable, then the flow may move to the determining whether to end treatment step 412. If the health check is favorable, then the flow may move to the modifying treatment step 410.

The health check may also include a check of the health of the system delivering treatment. For example, a detection of a clog in the system may result in an unfavorable health check. As another example, if a modification of treatment has not resulted in a desired, predicted, or expected change in sensor readings, there may be a problem with the system that may result in an unfavorable health check.

The continuing treatment step 410 may involve continuing treatment at current levels or modifying treatment. The modification of treatment may be based on the difference between the sensor readings and the target (as may be performed as part of step 406), the health check of step 408, the determination as to whether to end treatment 412, or other factors. Various parameters of treatment may be modified, including but not limited to those already described in the updating parameter step 314 described above. Following the modifying treatment step 410, the flow may move to step 404.

The determining whether to end treatment step may 412 be reached following either an unfavorable health check in step 408 or the reaching of a target in step 406. If the target is reached and there are no more targets to achieve, then this step 412 may result in a decision end treatment. If this step 412 is reached as a result of an unfavorable health check, then treatment may need to be ended, for example, depending on the severity of the unfavorability of the health check. For example, if the results of the health check indicate a slight trend toward a negative health state (e.g., an increase in intracranial pressure that may be the precursor of a headache), then the decision may be made to continue treatment but without increasing a treatment rate (e.g., the rate of cooling or the rate of rewarming), at a decreased treatment rate, at a maintained treatment rate.

The stopping treatment step 414 may be reached from the decision in step 412 to end treatment. Once treatment is stopped, various post-treatment wrap-up steps may be performed, including but not limited to those described above in reference to step 316.

FIG. 18 illustrates an example target cooling pattern for CSF. In particular, at time $t_0$, the temperature is initial temperature $T_i$. The CSF is then cooled. As illustrated, the CSF is cooled until it reaches the target temperature $T_t$ at a target time $t_1$. The CSF is then maintained at the target temperature $T_t$ until time $t_2$. Then the target temperature $T_t$ is maintained until time $t_2$. From time $t_2$ to the time $t_3$ the fluid is warmed to or allowed to warm to a final temperature $T_f$. The cooling and re-warming gradients may be managed by the method described in FIG. 18. Other cooling patterns are contemplated as being within the scope of the invention, with different slopes, transitions, lengths of time, temperature adjustments, etc.

For example, the target temperature $T_t$ may include, but need not be limited to, about 25° C. to about 35° C., about 25° C. to about 32° C., about 28° C. to about 32° C., about 29° C. to about 31° C., about 31° C., about 30° C., about 25° C., or other temperatures. The time from an initial time $t_0$ to a target time $t_1$ may include, but need not be limited to, about 50 minutes to about 70 minutes, about 60 minutes, about 30 minutes, about 5 minutes, about 10 seconds to about 40 seconds, about 20 seconds to 30 seconds, or other periods of time. The target temperature $T_t$ may be maintained until time $t_3$, which may include, but need not be limited to, about 50 minutes to about 70 minutes, about 60 minutes, about 30 minutes, about 5 minutes, about 10 seconds to about 40 seconds, or about 20 seconds to about 30 seconds from the time that target time $t_1$ was reached. The fluid may then be warmed to or allowed to warm to a final temperature $T_f$, which may include, but need not be limited to, the initial temperature $T_i$, average human body temperature (approximately 37° C.), or other temperatures. The time from time $t_2$ to time $t_3$ may include, but need not be limited to, about 50 minutes to about 70 minutes, about 60 minutes, about 30 minutes, about 5 minutes, about 10 seconds to about 40 seconds, about 20 seconds to about 30 seconds, or for other periods of time.

In some embodiments, the treatment period may be approximately 48 hours. For example, in embodiments directed toward subjects with traumatic brain injury, the total treatment time may be approximately 48 hours. This treatment length may result in a reduction in cytokine levels by more than 99% from a baseline in a system having flow rates of approximately 120 milliliters per hour.

Example Usage

Target Cooling Pattern. In an embodiment applying the target cooling pattern of FIG. 18 to the method of FIG. 17, time $t_0$ is 0 minutes, initial temperature $T_i$ is about 37° C., target temperature $T_t$ is about 30° C., target time $t_1$ is about 60 minutes, time $t_2$ is about 120 minutes ($t_2$-$t_1$=about 60 minutes), final temperature $T_f$ is about 37° C., and $t_3$ is about 180 minutes ($t_3$-$t_2$=about 60 minutes). In some embodiments, the system 100 may have predefined modes to initiate mild, moderate, or deep hypothermia; maintain temperature; monitor changes in pressure, flow, and temperature to ensure that the system is functioning properly; and manage the cooling and draining status of the subject 101. In some embodiments, the target temperature may vary based on location of measurements. For example, during hypothermia the core brain temperature may be maintained between about 28 to about 31° C., in accordance with the cold saline infusing speed. After cooling begins, the deep brain temperature will decrease to about 28° C. and the subcortical brain temperature may reach approximately 31° C. This temperature gradient between the brain surface and the deep brain may vary based on blood supply. In some embodiments, multiple temperature sensors may be used (e.g., located on the catheter) and an average brain temperature may be used based on the individual temperature probes. In some embodiments, if a clinician is trying to induce deep hypothermia (e.g., about 25 to about 30° C.) in the subject, then the system may measure parenchyma temperature and either continue cooling or maintain temperature based on the measured temperature. If the clinician is trying to revive the patient, then a re-warming algorithm may be engaged.

Walking through the method 400 of FIG. 17, the starting step 402 may begin at time $t_0$. At step 404, the system reads sensors and determines, inter alfa, that the initial temperature is about 37° C. At step 406, the determination is that this is not the target temperature $T_t$ of about 30° C. The flow moves to step 408 where a favorable health check based on intracranial pressure and EEG sensor data moves the flow to step 410. In step 410, the flow rate of heat transfer fluid through a catheter inserted into the spinal CSF space of the subject is increased. The loop of steps 404, 406, 408 and 410 continues until a target rate is reached (e.g., the cooling rate is such that the target temperature $T_t$ will be reached at approximately target time $t_1$). The loop then continues until the current time t is the target time $t_1$, which results in the determination that the target time and temperature has been reached at step 406, so the flow moves to the determination as to whether to end treatment at step 412. While this target was reached, all targets have not been reached, so the treatment continues and the flow moves to step 410. At step 410, the cooling rate is changed so the temperature T remains relatively constant through time $t_2$. The loop of steps 404, 406, 408 and 410 then continues until the current time t is time $t_2$. With this target reached, treatment is still not over, so the flow moves from step 406 to step 412 to step 410, where the treatment is modified so the temperature T increases at a rate such that it will reach final temperature $T_f$ at time $t_3$. Once these targets are met, treatment ends.

CSF Cooling Cycle (Spinal Portion). FIGS. 19-21 illustrate systems and methods for withdrawing, cooling, and returning CSF in a spinal region according to some embodiments. In particular, FIG. 19 illustrates CSF being withdrawn from a target lumbar cistern 504 using a first plurality of ports 132 of a catheter 130, the withdrawn CSF being processed in a treatment unit 106 to cool or otherwise treat the CSF, and the treated CSF being returned to a target cervicothoracic junction 502 using a second plurality of ports 134 of the catheter 130. FIG. 20 illustrates portions of the catheter 130, including regions where the first and second plurality of ports 132, 134 may be disposed. FIG. 21 illustrates a cross section of the catheter 130, including an inlet lumen 212 and an outlet lumen 216. CSF that is being withdrawn through the first ports 132 may pass through the inlet lumen 212 and CSF being returned through the second plurality of ports 134 may pass through the outlet lumen 216.

The treatment cycle may begin with the withdrawal of CSF from near a treatment site 202 using a first plurality of ports 132 of an elongate catheter 130. The catheter 130 may be deployed such that the first plurality of ports 132 is located within the target lumbar cistern 504 and second plurality of ports 134 is located within the target cervicothoracic junction 502. The target lumbar cistern 504 may be located in a region near the L2, L3, and L4 lumbar vertebrae; however, other target locations may also be used. The target cervicothoracic junction 502 may be located in a region near the C7, T1, T2, T3, and T4 vertebrae, though other locations may be used. Next, the CSF passes through the inlet lumen 212 of the catheter 130 and enters the treatment unit 106 through a port 108. Next, a sensor 114 may read the pressure of the CSF as the CSF passes through a pump 116. The pressure of the CSF is taken again using a sensor 114 as the fluid moves towards a temperature control unit 110. The temperature control unit 110 may modify the temperature of the withdrawn CSF. For example, the temperature control unit 110 may cool or warm the CSF. After the CSF leaves the temperature control unit 110, the CSF passes through a sensor 114 configured to read the pressure of the CSF and a sensor 114 configured to read the flow rate of the CSF. Next, the CSF passes through the port 108, the outlet lumen 116 of the catheter 130, and leaves the catheter 130 through the second plurality of ports 134 in the target cervicothoracic junction 502. The withdrawal and return of CSF may cause focal cooling of the spinal cord, a target treatment site 102. The control and management of this CSF cooling cycle may be controlled and monitored by a processing unit 118 and/or an interface 120. These components 118, 120 may be connected to the other components of the treatment unit 106.

CSF Cooling Cycle (Cerebral Ventricle). FIGS. 22-24 illustrate systems and methods for withdrawing, cooling, and returning CSF in a cerebral ventricle, a treatment site 202. In particular, FIG. 22 illustrates CSF being withdrawn from a target cerebral ventricle using a first plurality of ports 132 of a catheter 130, CSF being processed in a treatment unit 106 to cool or otherwise treat the CSF, and treated CSF being returned to the cerebral ventricle using a second plurality of ports 134 of the catheter 130. FIG. 23 illustrates portions of the catheter 130, including regions where the first and second plurality of ports 132, 134 may be disposed. FIG. 24 illustrates a cross section of the catheter 130, including an inlet lumen 212 and an outlet lumen 216. CSF may pass through the inlet lumen 212 after the CSF has been withdrawn through the first ports 132. CSF being returned through the second plurality of ports 134 may pass through the outlet lumen 216. The treatment process may be substantially similar to the process described with regard to FIGS. 19-21.

Cooling and CSF Filtration Cycle (Spinal Portion). FIGS. 25-27 illustrate methods and systems for withdrawing, filtering, and returning CSF in a spinal portion and cooling the spinal portion. In particular, FIG. 25 illustrates CSF being withdrawn from a target lumbar cistern 504 using a first plurality of ports 132 of a catheter 130, CSF being filtered by a filter 112 in a treatment unit 106, and filtered CSF being returned to a target cervicothoracic junction 502 using a second plurality of ports 134 of the catheter 130. The embodiment further provides cooling of a treatment site 102 using a temperature control unit 110 for cooling a heat transfer fluid that flows within the catheter 130 to change the temperature of the treatment site 102. FIG. 26 illustrates portions of the catheter 130, including regions where the first and second plurality of ports 132, 134 may be disposed. FIG. 21 illustrates a cross section of the catheter 130, including an inlet lumen 212, a cooling lumen 214, and an outlet lumen 216. CSF may pass through the inlet lumen 212 after the CSF has been withdrawn through the first ports 132. CSF being returned through the second plurality of ports 134 may pass through the outlet lumen 216. Heat transfer fluid may pass through the cooling lumen 214.

The cycle may begin with the withdrawal of CSF from near a treatment site 202 using a first plurality of ports 132 of an elongate catheter 130. The catheter 130 may be deployed such that the first plurality of ports 132 is located within the target lumbar cistern 504 and second plurality of ports is located within the target cervicothoracic junction 502. Other suitable locations may be used. The CSF passes through the inlet lumen 212 of the catheter 130 and enters the treatment unit 106 through a port 108. Next, the CSF may pass through a sensor 114 configured to read the pressure of the CSF and then a pump 116. The pressure of the CSF is taken again using a sensor 114 as the fluid heads towards a filter 112. The filter 112 may separate one or more components from the CSF with the materials that were filtered out being deposited in a vessel 122 and the filtered CSF being returned to the spinal portion 140. In particular, after the CSF leaves the filter 112, the CSF passes through the port, the outlet lumen 116 of the catheter 130, leaves the catheter 130 through the second plurality of ports 134 in the target cervicothoracic junction 502.

The vessel 122 may be a container for storing fluid. For example, fluid leaving the filter 112 may be deposited in the vessel 122. The fluid deposited in the vessel 122 may be held for storage, waste disposal, processing, testing, or other uses. The vessel 122 may also be a reservoir for subsequent filtering, cooling, or other processing for example, through the same or different set of filters. This fluid may or not be combined with previously filtered fluid Before, during, or after the filtration of the CSF, a temperature control unit 110 may cool or warm a volume of a heat transfer fluid. The heat transfer fluid may then flow within the cooling lumen 214 of the catheter 130 to cause cooling at the treatment site 102.

Cooling and CSF Filtration Cycle (Cerebral Ventricle). FIGS. 28-30 illustrate embodiments of systems and methods for withdrawing, filtering, and returning CSF in a cerebral ventricle. In particular, FIG. 28 illustrates an embodiment of CSF being withdrawn from a cerebral ventricle using a first plurality of ports 132 of a catheter 130 and filtered by a filter 112 in a treatment unit 106, with the filtered CSF being returned to the cerebral ventricle using a second plurality of ports 134 of the catheter 130. The embodiment further provides cooling of a treatment site 102 using a temperature control unit 110 for cooling a heat transfer fluid that flows within the catheter 130 to change the temperature of the treatment site 102. FIG. 29 illustrates portions of the catheter 130, including regions where the first and second plurality of ports 132, 134 may be disposed. FIG. 30 illustrates a cross section of the catheter 130, including an inlet lumen 212, a cooling lumen 214, and an outlet lumen 216. CSF that is being withdrawn through the first ports 132 may pass through the inlet lumen 212 and CSF being returned through the second plurality of ports 134 may pass through the outlet lumen 216. Heat transfer fluid may pass through the cooling lumen 214. The treatment process may be substantially similar to the process described with regard to FIGS. 25-27.

Cooling and Draining CSF Cycle (Spinal Portion). FIGS. 31-33 illustrate embodiments of systems and methods for draining CSF from a spinal portion and cooling the spinal portion. In particular, FIG. 31 illustrates CSF being withdrawn from a target lumbar cistern 504 and/or a target cervicothoracic junction using a first and/or second plurality of ports 132, 134 of a catheter 130 and the withdrawn CSF being deposited in a vessel 122. As with all embodiments, any suitable location may be used. The embodiment further provides cooling of a treatment site 102 using a temperature control unit 110 to cooling a heat transfer fluid that flows within the catheter 130 to change the temperature of the treatment site 102. FIG. 32 illustrates portions of the catheter 130, including regions where the first and second plurality of ports 132, 134 may be disposed. FIG. 33 illustrates a cross section of the catheter 130, including an inlet lumen 212 and three cooling lumens 214. Withdrawn CSF may pass through the inlet lumen 214. Heat transfer fluid may pass through the cooling lumen 214.

The cycle may begin with the withdrawal of CSF from at or near a treatment site 202 using a first and/or second plurality of ports 132, 134 of an elongate catheter 130. The catheter 130 may be deployed such that the first plurality of ports 132 is located within the target lumbar cistern 504 and second plurality of ports is located within the target cervicothoracic junction 502. The CSF passes through the inlet lumen 212 of the catheter 130 and enters the treatment unit 106 through a port 108. Next, the CSF may pass through a sensor 114 configured to read the pressure of the CSF and then a pump 116. The CSF is then deposited in a vessel 122.

Before, during, or after the filtration of the CSF, a temperature control unit 110 may cool or warm a volume of a heat transfer fluid. The heat transfer fluid may then flow within the cooling lumen 214 of the catheter 130 to cause cooling at the treatment site 102. The heat transfer fluid may pass through a sensor 114 configured to read the fluid's pressure and a sensor 114 to read the fluid's flow rate.

Cooling and Draining CSF Cycle (Cerebral Ventricles). FIGS. 34-36 illustrate embodiments of systems and methods for draining CSF from a cerebral ventricle and cooling the cerebral ventricle. In particular, FIG. 34 illustrates CSF being withdrawn from a cerebral ventricle using a first and/or second plurality of ports 132, 134 of a catheter 130 and the withdrawn CSF being deposited in a vessel 122. The embodiment further provides cooling of a treatment site 102 using a temperature control unit 110 for cooling a heat transfer fluid that flows within the catheter 130 to change the temperature of the treatment site 102. FIG. 35 illustrates portions of the catheter 130, including regions where the first and second plurality of ports 132, 134 may be disposed. FIG.

Figure 37:
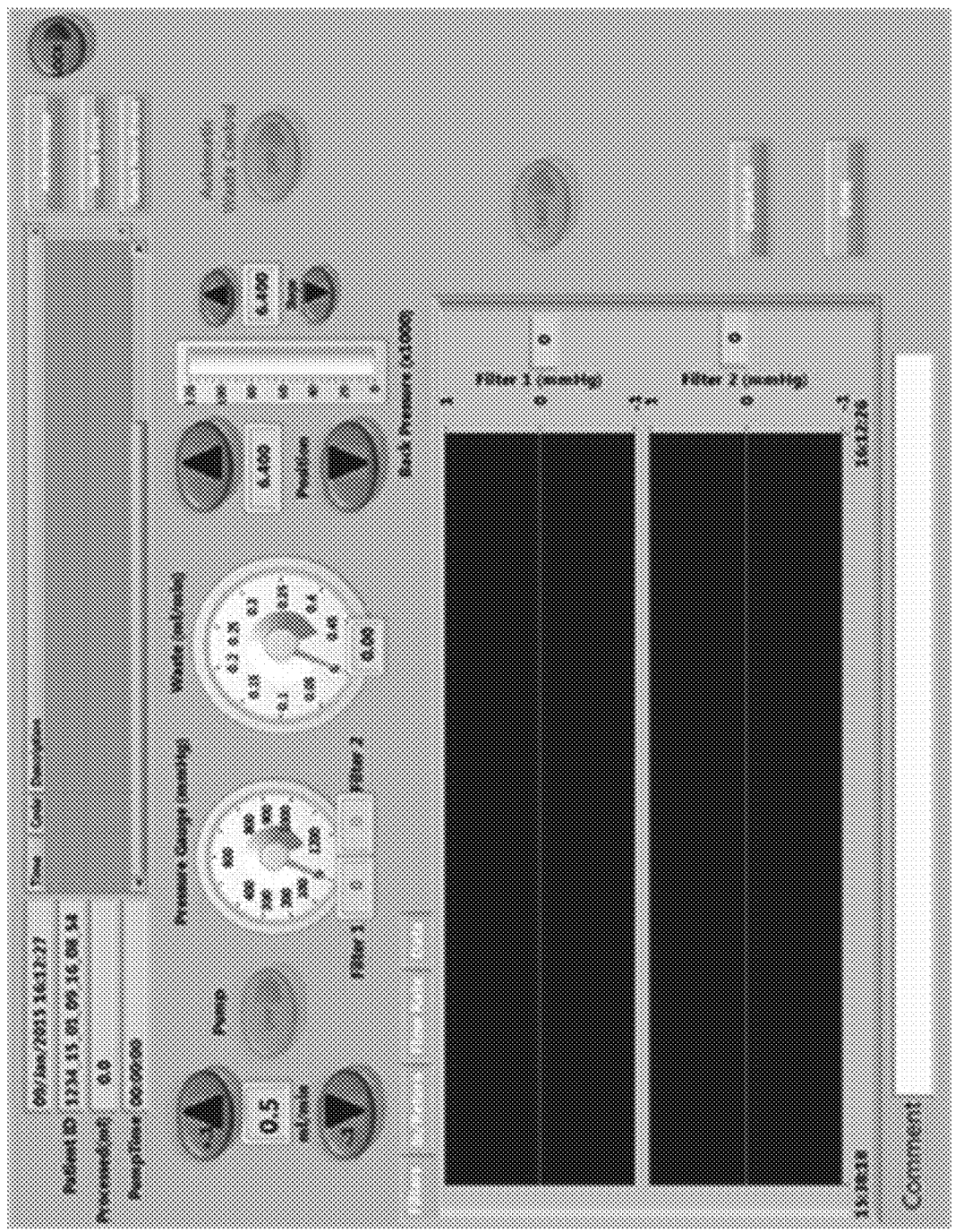
FIG. 37 illustrates an example user interface that may be used in one or more embodiments of the invention.

36 illustrates a cross section of the catheter 130, including an inlet lumen 212 and three cooling lumens 214. Withdrawn CSF may pass through the inlet lumen 214. Heat transfer fluid may pass through the cooling lumen 214. Before, during, or after the filtration of the CSF, a temperature control unit 110 may cool or warm a volume of the heat transfer fluid to cause cooling at the treatment site 102. The treatment process may be substantially similar to the process described with regard to FIGS. 31-33. User Interface. FIG. 37 illustrates an example user interface that may be used in conjunction with one or more disclosed embodiments. The user interface may include, among other things, a patient identifier, a measurement of the amount of CSF that has been processed, a length of time that a pump has been running, a listing of error codes (including a time, number, and description of the code), a graph and/or gauge of a pressure sensed at a filter, a graph and/or gauge of an amount of CSF that has been withdrawn from the subject, a graph and/or gauge of a measured flow rate, a graph and/or gauge of the amount of fluid that has flown to a waste vessel, a graph and/or gauge of the rate at which material is being deposited within the vessel, a stream of raw data from sensors, and other information as desired. The user interface may also contain various controls, such as controls for turning on or off a pump, changing how quickly fluid flows through the system (e.g., by changing a parameter of the pump), increasing or decreasing position and/or step parameters of a back pressure device, locking or unlocking the system, turning on or off automatic waste control, setting a tare, leaving a comment, and/or performing other operations.

EXPERIMENTAL

Figure 38:
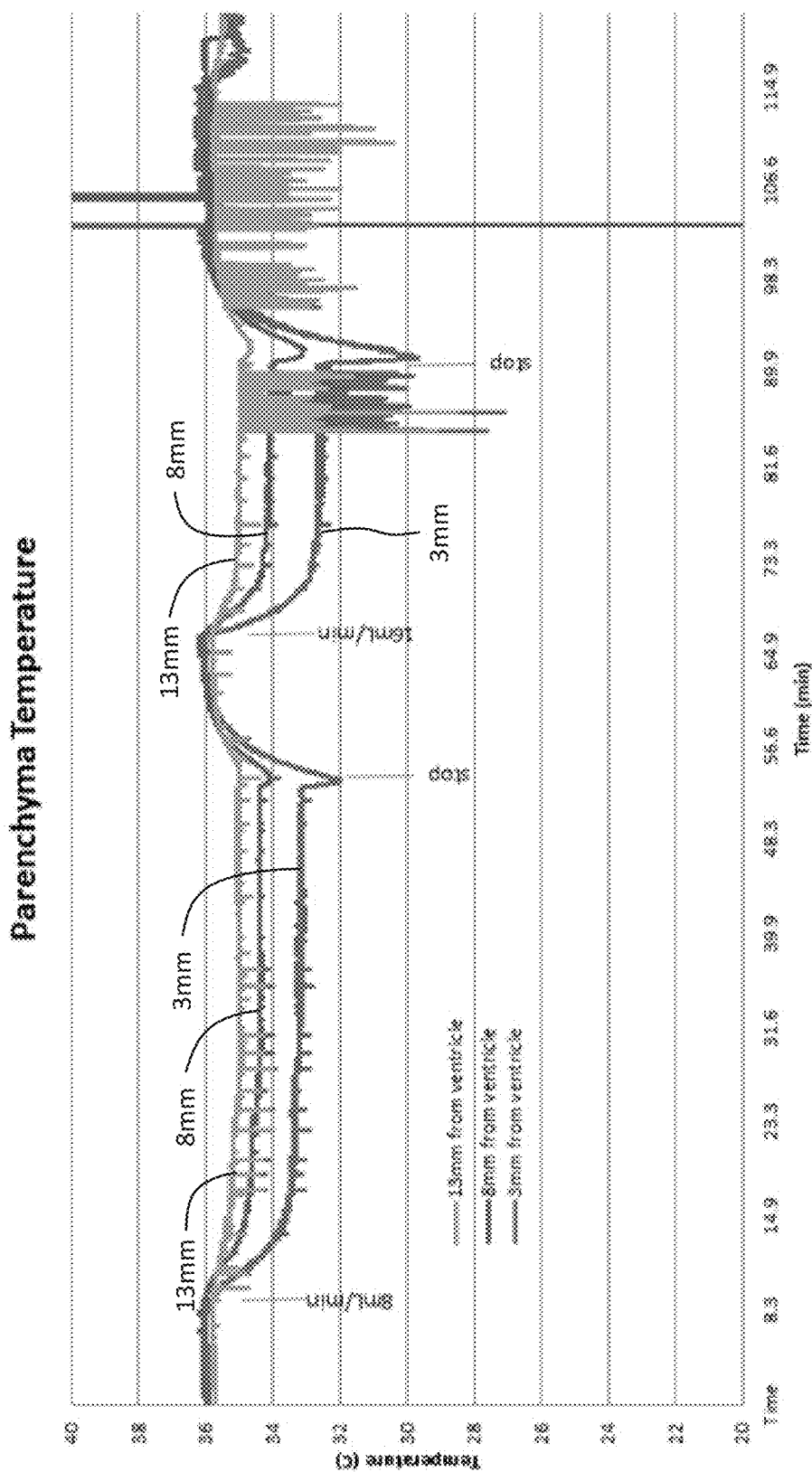
FIG. 38 illustrates measured brain parenchyma temperature during a CSF cooling study in a bovine subject.

FIG. 38 illustrates measured brain parenchyma temperature during a CSF cooling study in a bovine subject. Temperature of the brain parenchyma was measured at a distance of 3 mm from a cerebral ventricle, 8 mm from the ventricle, and 13 mm from the ventricle over a period of time. In the study, CSF of the bovine subject was withdrawn using a dual-lumen catheter, chilled with a chiller, and returned to the subject using the catheter. The study included the use of 3-on-1 temperature sensors.

As illustrated, at approximately 8.3 minutes, the flow rate of the CSF was 8 ml/min, which caused a measurable drop in the temperature of the parenchyma. At approximately 53 minutes, the flow rate was stopped and the temperature of parenchyma increased to approximately 36° C. at 3 mm, 8 mm, and 13 mm from the ventricle. At approximately 66 minutes, the flow rate was set to 16 ml/min, which caused a measurable drop in the temperature of the parenchyma. The flow rate of 16 ml/min caused the temperature to drop approximately twice as fast as the flow rate of 8 ml/min. At approximately 90 minutes, the flow rate was stopped and the temperature rose.

The study shows a statistically significant decrease in brain temperature even 13 mm from the ventricle using a CSF cooling technique. In this manner, CSF cooling techniques can be used to cool brain parenchyma and can present advantages compared to surface cooling.

Figure 39:
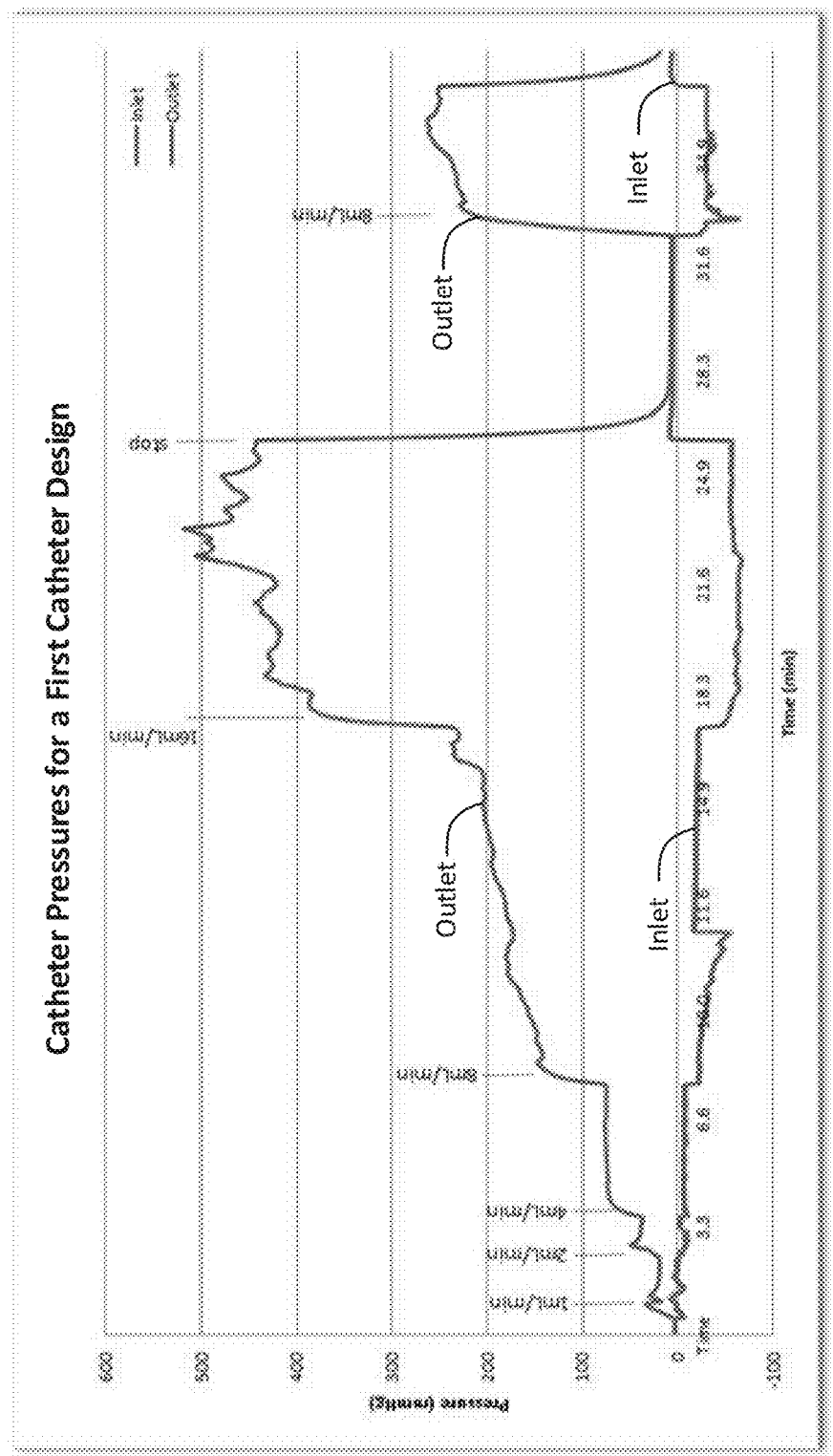
FIG. 39 illustrates measured inlet and outlet pressure within a catheter over time and over a variety of CSF flow rates for a first catheter design.

FIG. 39 illustrates measured inlet and outlet pressure within a catheter over time and over a variety of CSF flow rates for a first catheter design. As illustrated, the catheter outlet pressure increases as the flow rate of the catheter increases from 1 ml/min to 16 ml/min.

Figure 40:
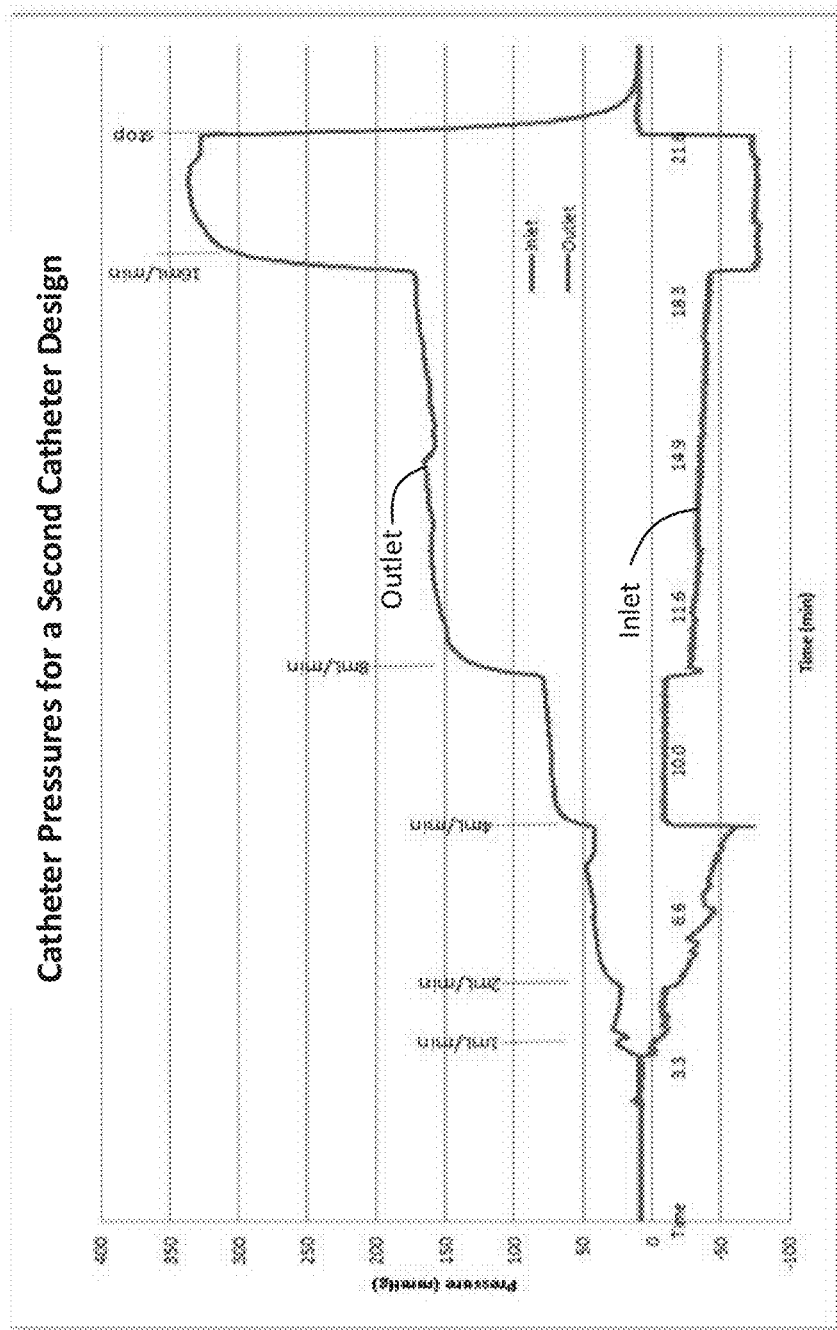
FIG. 40 illustrates measured inlet and outlet pressure within a catheter over time and over a variety of CSF flow rates for a second catheter design.

FIG. 40 illustrates measured inlet and outlet pressure within a catheter over time and over a variety of CSF flow rates for a second catheter design. As illustrated, the catheter outlet pressure increases as the flow rate of the catheter increases from 1 ml/min to 16 ml/min.

It can be advantageous to keep catheter pressure below 500 mmHg for safe operation of the catheter.

Within this disclosure, connection references (for example, attached, coupled, connected, and joined) may include intermediate members between a collection of components and relative movement between components. Such references do not necessarily infer that two components are directly connected and in fixed relation to each other. The exemplary drawings are for purposes of illustration only and the dimensions, positions, order and relative sizes reflected in the drawings attached hereto may vary.

The above specification provides a complete description of the structure and use of exemplary embodiments as claimed below. Although various embodiments of the invention as claimed have been described above with a certain degree of particularity, or with reference to one or more individual embodiments, those skilled in the art could make numerous alterations to the disclosed embodiments without departing from the spirit or scope of this disclosure. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the disclosure as defined in the following claims.

What is claimed is:

1. A method for providing focal cooling at a treatment site of a human or animal subject using a treatment system to treat a subarachnoid hemorrhage, a thoraco-abdominal aortic aneurysm, a fever, a seizure condition, an intracerebral hemorrhage, cerebral ischemia, hydrocephalus, a cerebrospinal fluid (CSF) leak, a traumatic brain injury, or inflammation, the method comprising:
deploying a catheter at or near the treatment site;
withdrawing CSF near the treatment site through an inlet lumen of the catheter;
reducing the temperature of the withdrawn CSF;
returning the withdrawn CSF to the subject;
measuring a rate of temperature change at the treatment site using a sensor;
comparing the measured rate of temperature change with a target rate of temperature change; and
modifying a treatment parameter if the rate of temperature changes differs from the target rate of temperature change.

2. The method of claim 1, wherein the treatment site comprises at least one of brain parenchyma of the subject or spinal cord tissue of the subject.

3. The method of claim 1, further comprising filtering the withdrawn CSF.

4. The method of claim 3, further comprising filtering cytokines from the withdrawn CSF.

5. The method of claim 1, wherein the treatment parameter is a rate at which the CSF is withdrawn, a rate at which CSF is returned, or a temperature to which the temperature of the CSF is reduced.

6. A method for providing focal cooling at a treatment site of a human or animal subject using a treatment system to treat a subarachnoid hemorrhage, a thoraco-abdominal aortic aneurysm, a fever, a seizure condition, an intracerebral hemorrhage, cerebral ischemia, hydrocephalus, a cerebrospinal fluid (CSF) leak, a traumatic brain injury, or inflammation, the method comprising:

deploying a catheter at or near the treatment site;

passing a heat transfer fluid through a lumen of the catheter;

measuring a rate of temperature change at the treatment site using a sensor;

comparing the measured rate of temperature change with a pre-determined target rate of temperature change;

modifying a treatment parameter when the measured rate of temperature change differs from the pre-determined target rate of temperature change.

7. The method of claim 6, wherein the method further comprises placing an outer surface of an inflatable section of the catheter in proximal contact with tissue near the treatment site by inflating the inflatable section, the outer surface comprising a cooling section configured to facilitate the cooling of the tissue by the heat transfer fluid.

8. The method of claim 7, wherein inflating the inflatable section comprises filling the inflatable section with heat transfer fluid.

9. The method of claim 7, wherein the outer surface of the inflatable section comprises a pathway through which the heat transfer fluid flows.

10. The method of claim 6, wherein the characteristic is temperature, intracranial pressure, or electrical activity.

11. The method of claim 6, wherein the treatment site comprises at least one of brain parenchyma of the subject or spinal cord tissue of the subject.

12. The method of claim 6, further comprising withdrawing CSF at or near the treatment site through an inlet lumen of the catheter.

13. The method of claim 12, further comprising filtering the withdrawn CSF.

14. The method of claim 12, further comprising reducing the temperature of the withdrawn CSF and returning the withdrawn CSF through an outlet lumen of the catheter.

15. The method of claim 14, wherein the treatment parameter is a rate at which the CSF is withdrawn, a rate at which CSF is returned, or a temperature to which the temperature of CSF is reduced.

16. A method for providing focal cooling, the method comprising:

disposing a catheter adjacent to a target location;

withdrawing cerebrospinal fluid from the target location through an inlet lumen of the catheter;

cooling the withdrawn cerebrospinal fluid;

returning the cooled cerebrospinal fluid to the target location;

measuring a rate of temperature change at the treatment site using a sensor;

comparing the rate of temperature change with a pre-determined target rate of temperature change; and modifying a flow rate at which the cooled cerebrospinal fluid is returned to the target location if the rate of temperature changes differs from the target rate of temperature change.

17. The method of claim 16, further comprising filtering the withdrawn cerebrospinal fluid.

18. The method of claim 16, wherein modifying a flow rate at which the cooled cerebrospinal fluid is returned to the target location if the rate of temperature changes differs from the target rate of temperature change includes reducing the flow rate at which the cooled cerebrospinal fluid is returned to the target location.

19. The method of claim 16, wherein modifying a flow rate at which the cooled cerebrospinal fluid is returned to the target location if the rate of temperature changes differs from the target rate of temperature change includes increasing the flow rate at which the cooled cerebrospinal fluid is returned to the target location.

* * * * *